US010322206B2

(12) United States Patent
Pins et al.

(10) Patent No.: US 10,322,206 B2
(45) Date of Patent: Jun. 18, 2019

(54) COMPOSITIONS AND METHODS FOR WOUND HEALING

(71) Applicants: George Pins, Worcester, MA (US);
Glenn Gaudette, Worcester, MA (US);
Adam Collette, Worcester, MA (US);
William Edelman, Worcester, MA (US)

(72) Inventors: George Pins, Worcester, MA (US);
Glenn Gaudette, Worcester, MA (US);
Adam Collette, Worcester, MA (US);
William Edelman, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 15/472,330

(22) Filed: Mar. 29, 2017

(65) Prior Publication Data

US 2017/0281825 A1    Oct. 5, 2017

Related U.S. Application Data

(60) Provisional application No. 62/314,431, filed on Mar. 29, 2016.

(51) Int. Cl.
*A61L 17/08* (2006.01)
*A61L 17/10* (2006.01)
*A61L 17/12* (2006.01)

(52) U.S. Cl.
CPC .............. *A61L 17/08* (2013.01); *A61L 17/10* (2013.01); *A61L 17/12* (2013.01)

(58) Field of Classification Search
CPC ........... A61L 17/08; A61L 17/10; A61L 17/12
See application file for complete search history.

(56) References Cited

U.S. PATENT DOCUMENTS

| | | | |
|---|---|---|---|
| 4,001,459 A | 1/1977 | Kim et al. | |
| 4,683,142 A | 7/1987 | Zimmerman et al. | |
| 4,874,368 A | 10/1989 | Miller et al. | |
| 4,880,002 A | 11/1989 | MacGregor | |
| 6,054,122 A | 4/2000 | MacPhee et al. | |
| 6,331,422 B1 | 12/2001 | Hubbell et al. | |
| 6,352,710 B2 | 3/2002 | Sawhney et al. | |
| 6,552,172 B2 | 4/2003 | Marx et al. | |
| 6,749,617 B1 | 6/2004 | Palasis et al. | |
| 6,955,681 B2 | 10/2005 | Evans et al. | |
| 7,084,082 B1 | 8/2006 | Shimizu | |
| 7,686,799 B2 | 3/2010 | Leonhardt et al. | |
| 7,759,082 B2 | 7/2010 | Bowlin et al. | |
| 8,454,653 B2* | 6/2013 | Hadba .............. | A61B 17/06166 606/228 |
| 8,585,753 B2 | 11/2013 | Scanlon et al. | |
| 8,865,869 B2 | 10/2014 | Cornwell et al. | |
| 9,662,415 B2 | 5/2017 | Cornwell et al. | |
| 2001/0045177 A1 | 11/2001 | Harvey et al. | |
| 2002/0042128 A1 | 4/2002 | Bowlin | |
| 2002/0055759 A1 | 5/2002 | Shibuya | |
| 2002/0107430 A1 | 8/2002 | Neisz et al. | |
| 2002/0168398 A1 | 11/2002 | Delmotte | |
| 2003/0021777 A1 | 1/2003 | Harris et al. | |
| 2003/0203008 A1 | 10/2003 | Gunasekaran | |
| 2005/0125035 A1 | 6/2005 | Cichocki | |
| 2006/0029578 A1 | 2/2006 | Hoemann et al. | |
| 2006/0047312 A1 | 3/2006 | Garcia Olmo et al. | |
| 2011/0034388 A1* | 2/2011 | Cornwell .............. | A61L 27/225 514/13.6 |
| 2013/0096610 A1 | 4/2013 | Pins et al. | |
| 2015/0005739 A1 | 1/2015 | Gaudette et al. | |
| 2015/0025009 A1 | 1/2015 | Cornwell et al. | |

FOREIGN PATENT DOCUMENTS

| | | |
|---|---|---|
| CN | 101797377 | 11/2010 |
| EP | 0463887 | 1/1992 |
| WO | 2007109137 | 9/2007 |
| WO | 2008116189 | 9/2008 |
| WO | 2011112976 | 9/2011 |
| WO | 2011116250 | 9/2011 |
| WO | 2015148993 | 10/2015 |

OTHER PUBLICATIONS

Muffly, The history and evolution of sutures in pelvic surgery, J R Soc Med 2011: 104: 107-112.*
Yedke, Experimental evaluation of horse hair as a nonabsorbable monofilament suture, J Ayurveda Integr Med. Oct.-Dec. 2013; 4(4): 206-210.*
Muffly, The history and evolution of sutures in pelvic surgery, J R Soc Med 2011: 104: 107-112, of record (Year: 2011).*
Yedke, Experimental evaluation of horse hair as a nonabsorbable monofilament suture, J Ayurveda Integr Med. Oct.-Dec. 2013; 4(4): 206-210, of record (Year: 2013).*
Cornwell, et al., "Discrete Crosslinked Fibrin Microthread Scaffolds for Tissue Regeneration," Journal of Biomedical Materials Research, Part A., 2007, vol. 82, No. 1, pp. 104-112.
Gui et al. "Identification of the Heparin-binding Determinants with Fibronectin Repeat III]" Journal of Biological Chemistry vol. 281 No. 46 pp. 34816-34825 Nov. 17, 2006.
Hocking et al. "Extracellular Matrix Fibronectin Mechanically Couples Skeletal Muscle Contraction With Local Vasodilation" Circulation Research vol. 102 pp. 372-379 2008.
International Search Report, for International Application No. PCT/US2017/024654, dated Jul. 13, 2017, 8 pages.
(Continued)

*Primary Examiner* — Karlheinz R. Skowronek
*Assistant Examiner* — Khalid Kader
(74) *Attorney, Agent, or Firm* — Morgan, Lewis & Bockius LLP

(57) ABSTRACT

The present invention relates, in part, to sutures which promote wound closure and/or healing. In particular, the present invention provides fibrin microthread sutures that mimic the mechanical behavior of a target tissue thereby reducing, for example, scarring, inflammation, and cell death at the ligature site, including monofilament sutures.

15 Claims, 4 Drawing Sheets

(56) References Cited

OTHER PUBLICATIONS

Lewis, et al., "Fixtation of Tissue-Engineered Human Neocartilage Constructs with Human Fibrin in a Caprine Model", J Knee Surg., 2009, vol. 22, pp. 196-204.
Muffly, The History and Evolution of Sutures in Pelvic Surgery, JR Soc Med 2011, vol. 104, pp. 107-112.
Yedke, Experimental Evaluation of Horse Hair as a Nonabsorbabie Monofilament Sulture, J Ayurveda Integr Med., 2013, vol. 4, No. 4 pp. 206-210.

* cited by examiner

COMPOSITIONS AND METHODS FOR WOUND HEALING

CROSS REFERENCE TO RELATED APPLICATIONS

This application claims the benefit of U.S. Provisional Patent Application No. 62/314,431, filed Mar. 29, 2016, the entire contents of which are hereby incorporated by reference.

FIELD OF THE INVENTION

The present invention relates, in part, to sutures which promote wound closure and/or healing. In particular, the present invention provides fibrin microthread sutures that mimic the mechanical behavior of a target tissue thereby reducing, for example, scarring, inflammation, and cell death at the target tissue.

BACKGROUND

Multicellular organisms including mammals are made up of tissues which are organized aggregates of specialized groups of cells. When tissues become damaged, for example, from an injury, or a surgical procedure, physiological events take place to close and repair the damaged site (e.g., an open wound, a surgical incision, etc.), and allow successful repair and regeneration of the tissue. These physiological events include an inflammatory response in which neutrophils, eosinophils, macrophages, lymphocytes, fibrocytes, and other cells involved in the inflammatory response migrate to the damage site to promote blood clotting and remove bacteria, debris and damaged tissue. Later, circulating cells migrate to the wound site and differentiate into myofibroblasts. The differentiated cells begin to deposit new extracellular matrix, which includes a complex assemblage of proteins, carbohydrates, and collagen, that provide support and anchor for the cells. Depending on the method used to close and repair the wound, excessive connective tissue and collagen can be deposited on the damage site. This can cause fibrosis on the damage site leading to scars, which can be particularly undesirable in topical or cosmetic surgical procedures.

Sutures are often used to ligate or close an open wound resulting from, for example, an injury or an incision formed during a surgical procedure. However, state of the art conventional sutures, such as, for example, silk, linen, nylon, polypropylene, polyamide, polyester, cat gut, polyglycolic acid, polylactic acid, polydioxanone, poliglecaprone (MONOCRYL), polyglactin (VICRYL), and caprolactone sutures are often inflexible thus inducing mechanical stress on the surrounding tissues and causing inflammation, scarring, and tissue necrosis at the ligation site.

There remains a need for new sutures that provide lower inflammation, reduced scarring, less likelihood of infection, and reduced cell death in a target tissue.

SUMMARY OF THE INVENTION

Accordingly, the present invention provides compositions and methods for promoting wound closure and/or healing of a target tissue. The wound may be a, for example, a surgical wound or a trauma wound. In various embodiments, the target tissue is a soft tissue such as skin, tendon, ligament, fascia, fibrous tissue, fat, synovial membrane, and muscle, nerve and blood vessel.

Specifically, in some embodiments, the present invention provides methods for promoting wound closure and/or healing involving the application of a suture that mimics the mechanical behavior of the target tissue. In an embodiment, the suture exhibits a stiffness of about 5 MPa to about 20 MPa as measured by Young's modulus. In an embodiment, the suture exhibits a stiffness of less than about 15 MPa as measured by Young's modulus. In various embodiments, the suture mimics the elasticity of the target tissue.

In various embodiments, the suture comprises fibrin. In an embodiment, the suture comprises a fibrin microthread. The fibrin microthread may be associated with one or more of a substrate or a braided yarn or other hierarchically organized rope, a woven or non-woven mesh, a surgical needle, a surgical pin, a surgical screw, a surgical plate, a physiologically acceptable patch, a dressing, a bandage, or a natural or mechanical valve. In certain embodiments, the fibrin microthread includes an additional therapeutic agent. In certain embodiments, the additional therapeutic agent can be incorporated in the fibrin microthreads. The therapeutic agent can be incorporated in the fibrin microthread using any suitable process such as, for example, covalent bonding to the fibrin microthread, surface adsorption, or physical incorporation during the preparation of the fibrinogen or fibrin-forming solutions, during mixing of the fibrinogen and the molecule capable of forming fibrin, during post-formation adsorption while still in a forming buffer, or absorption during a subsequent hydration process.

The methods of the invention promote wound closure and/or healing. In certain embodiments, the method prevents or reduces excess collagen deposition in a target tissue. The method may improve the cosmetic appearance of scars at a target tissue. The method may also prevent or reduce hypertrophic scar formation or keloid formation at a target tissue. In certain embodiments, methods of the invention prevent or reduce the extent of cell death at a target tissue. The method may reduce persistent hypercellularity or inflammation at a target tissue. The method may also prevent or reduce pruritus or numbness at a target tissue. In various embodiments, surgical extrusion, wound dehiscence, incisional hernia, and/or occlusion are prevented or reduced by methods of the invention.

In various embodiments, methods of the invention may be combined with administration of steroid, silicone, vitamin, laser treatment, radiotherapy, pressure dressing, collagen induction therapy, cryotherapy, or dermabrasion.

BRIEF DESCRIPTION OF THE FIGURES

FIG. 1, panels A and B show automation of thread extrusion via a three axis thread extruder allows for consistent production of fibrin microthreads. FIG. 1, panels C and D show that microthreads produced in accordance with methods of the invention have consistent diameter (as measured using a yarn micrometer) and failure load (as measured via uniaxial pull to failure).

FIG. 2, panel A shows production differences between multi-filament and mono-filament fibrin microthread sutures. FIG. 2, panel B shows a scanning electron microscope (SEM) micrograph of multi-filament suture cross section. FIG. 2, panel C shows a SEM micrograph of mono-filament suture cross-section. (Scale bars 100 μm)

FIG. 3, panel A shows mechanical testing of fibrin microthreads. FIG. 3, panel B shows that fibrin microthread tensile strength increases with thrombin concentration. FIG. 3, panel C shows that fibrin microthread strength increases with addition of $CaCl_2$. FIG. 3, panel D shows that the addition of a stretching protocol and drying step increases microthread tensile strength. (*indicates p<0.05)

FIG. 4, panel A shows fibrin microthread sutures produced in six different form-factors and sizes. As shown, the sutures are associated with different needle sizes. Sutures can also be associated with consistently sized needles. FIG. 4, panel B show the schematics of fibrin microthread sutures implanted into a rat dorsal skin closure model. FIG. 4, panel C show the schematics of testing fibrin microthread sutures via biological assessment and wound mechanics.

DETAILED DESCRIPTION

Figure 1:
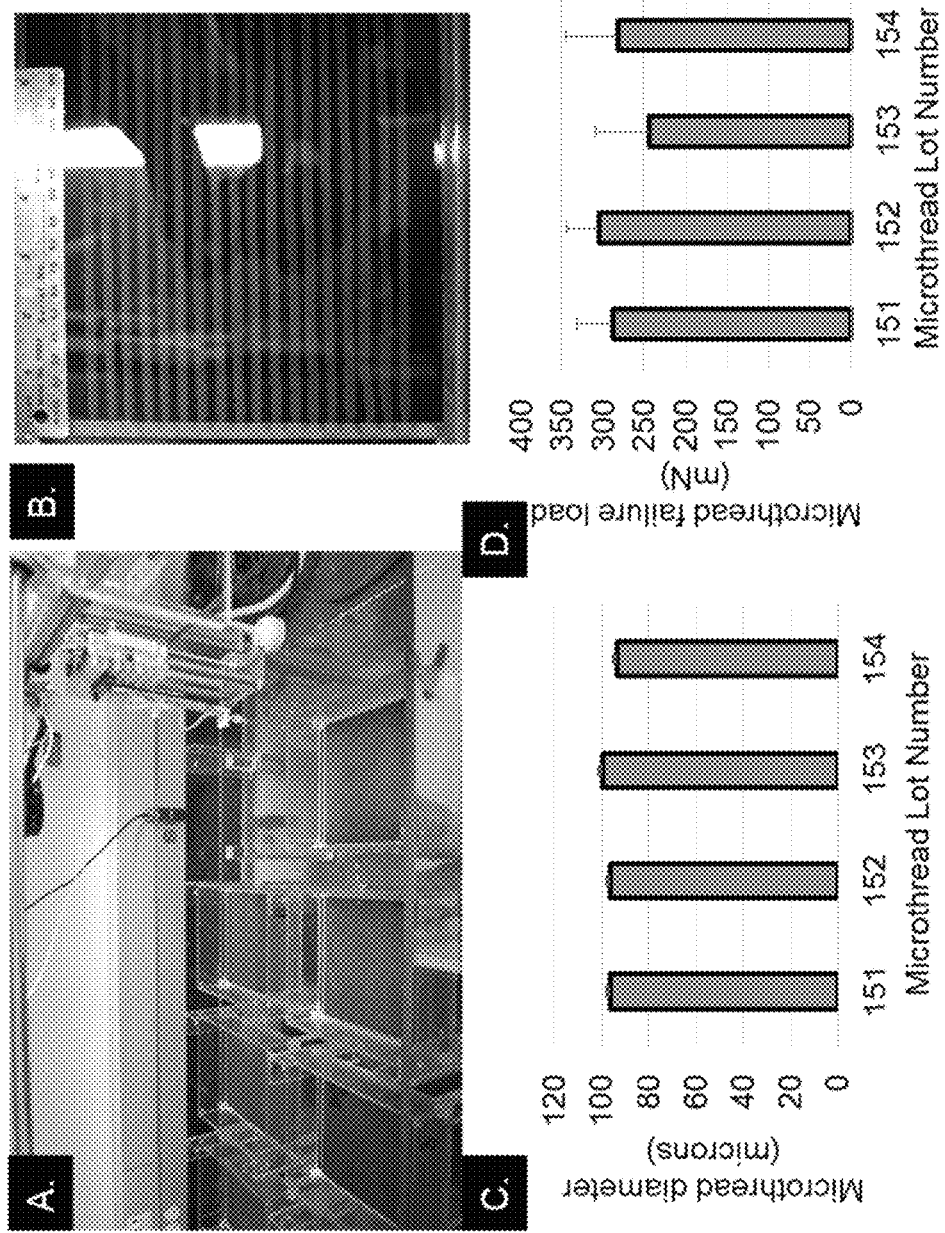
FIG. 1, panels A-D show the production of fibrin microthreads using a three axis electromechanical extrusion head.

The present invention is based, in part, on the discovery that fibrin microthread sutures that mimic the mechanical properties of a target tissue provide desirable wound closure characteristics that improve upon conventional suture technology. Embodiments described herein relate generally to sutures, and in particular to fibrin microthread sutures, that provide, for example, lower inflammation, reduced scarring, reduced likelihood of infection, and reduced cell death in a target tissue. Accordingly, the present invention provides, in part, various methods for wound closure with a fibrin microthread suture and/or uses of a fibrin microthread suture in wound closure and/or in the manufacture of a medicament for wound closure.

Fibrin Microthread Sutures

In various embodiments, the present invention provides a suture with fibrin microthread. Embodiments of the fibrin microthread suture described herein can overcome the limitations of conventional surgical sutures. Particularly, the fibrin microthread sutures of the present invention mimic the mechanical properties of a target tissue in which the sutures are implanted, thereby providing advantages over conventional suture including, for example: (a) substantially reduced collagen deposition at the ligation site leading to little or no fibrosis or scarring; (b) substantially reduced inflammation relative to conventional sutures; and (c) substantially reduced cell death (e.g., apoptosis or necrosis) relative to conventional sutures. Thus, embodiments of the fibrin microthread sutures described herein can be particularly beneficial for use as surgical sutures in high visibility and/or high sensitivity tissue ligation applications such as, for example, aesthetic surgery procedures.

The fibrin microthread sutures described herein exhibit mechanical properties similar to that of the target tissue in which it is implanted. In certain embodiments, the fibrin microthread sutures mimic the stiffness behavior of the target tissue. In an embodiment, the fibrin microthread sutures exhibit elasticity similar or identical to the target tissue. Stiffness may be measured, for example, by Young's modulus, otherwise known as tensile modulus or elastic modulus. It is defined as the ratio of the stress acting on a substance to the strain produced. Methods for determining the Young's modulus of a material are established in the art. For example, fibrin microthread sutures can be hydrated and mechanically loaded in uniaxial tension to obtain stress-strain curves, from which Young's modulus may be calculated.

In various embodiments, the fibrin microthread sutures of the invention mimic the stiffness behavior of a target tissue as measured by, for example, Young's modulus. Table 1 below provides an overview of the Young's moduli for a series of soft tissues.

TABLE 1

| Tissue Type | Failure Strain | Young's Modulus |
| --- | --- | --- |
| Skin | 17-207% | 7 KPa-150 MPa |
| Liver | | 0.4-0.6 KPa |
| Brain | | 0.1 KPa |
| Muscle | | 10 Kpa |
| Lungs | | 0.5-3 KPa |
| Smooth muscle (relaxed) | 300% | 6 KPa |
| Smooth muscle (contracted) | 300% | 10 KPa |
| Aorta (porcine) | | 440-658 Kpa |

In an embodiment, the fibrin microthread sutures may have a Young's modulus in the range of about 5 kPa to about 150 MPa. For example, the fibrin microthread sutures may have a Young's modulus in the range of from about 10 kPa to about 145 MPa, from about 10 kPa to about 140 MPa, from 10 kPa to about 135 MPa, from about 10 kPa to about 130 MPa, from about 10 kPa to about 125 MPa, from about 10 kPa to about 120 MPa, from about 10 kPa to about 115 MPa, from about 10 kPa to about 110 MPa, from about 10 kPa to about 105 MPa, from about 10 kPa to about 100 MPa, from about 10 kPa to about 95 MPa, from about 10 kPa to about 90 MPa, from about 10 kPa to about 85 MPa, from about 10 kPa to about 80 MPa, from about 10 kPa to about 75 MPa, from about 10 kPa to about 70 MPa, from about 10 kPa to about 65 MPa, from about 10 kPa to about 60 MPa, from about 10 kPa to about 55 MPa, from about 10 kPa to about 50 MPa, from about 10 kPa to about 45 MPa, from about 10 kPa to about 40 MPa, from about 10 kPa to about 35 MPa, from about 10 kPa to about 30 MPa, from about 10 kPa to about 25 MPa, from about 10 kPa to about 20 MPa, from about 10 kPa to about 15 MPa, from about 10 kPa to about 10 MPa, from about 10 kPa to about 5 MPa, from about 10 kPa to about 1 MPa, from about 1 MPa to about 50 MPa, from about 1 MPa to about 40 MPa, from about 1 MPa to about 30 MPa, from about 1 MPa to about 20 MPa, from about 1 MPa to about 10 MPa, from about 1 MPa to about 5 MPa, from about 5 MPa to about 50 MPa, from about 5 MPa to about 40 MPa, from about 5 MPa to about 30 MPa, or from about 5 MPa to about 20 MPa, inclusive of all values and ranges therebetween.

In certain embodiments, the fibrin microthread sutures may have a Young's modulus of less than about 150 MPa, about 145 MPa, about 140 MPa, about 135 MPa, about 130 MPa, about 125 MPa, about 120 MPa, about 115 MPa, about 110 MPa, about 105 MPa, about 100 MPa, about 95 MPa, about 90 MPa, about 85 MPa, about 80 MPa, about 75 MPa, about 70 MPa, about 65 MPa, about 60 MPa, about 55 MPa, about 50 MPa, about 45 MPa, about 40 MPa, about 35 MPa, about 30 MPa, about 25 MPa, about 20 MPa, about 15 MPa, about 14 MPa, about 13 MPa, about 12 MPa, about 11 MPa, about 10 MPa, about 9 MPa, about 8 MPa, about 7 MPa, about 6 MPa, about 5 MPa, about 4 MPa, about 3 MPa, about 2 MPa, or about 1 MPa, inclusive of all values and ranges therebetween.

The ultimate tensile strength (UTS) of the fibrin microthread sutures may vary according to size and the methods used for synthesis. Methods for measuring tensile strength are well-known to those of skill in the art. In various embodiments, the fibrin microthread sutures of the invention can have an UTS in the range of from about 0.5 MPa to about 250 MPa, about 1 MPa to about 200 MPa, about 1 MPa to about 150 MPa, about 1 MPa to about 100 MPa, from about 1 MPa to about 50 MPa, from about 1 MPa to about 45 MPa, from about 1 MPa to about 40 MPa, from about 1 MPa to about 35 MPa, from about 1 MPa to about 30 MPa, from about 1 MPa to about 25 MPa, from about 1 MPa to about 20 MPa, from about 1 MPa to about 15 MPa, from about 1 MPa to about 10 MPa, or from about 1 MPa to about 5 MPa, inclusive of all values and ranges therebetween.

In certain embodiments, the fibrin microthread sutures can have an UTS of about 0.5 MPa, about 0.6 MPa, about 0.7 MPa, about 0.8 MPa, about 0.9 MPa, about 1 MPa, about 2 MPa, about 3 MPa, about 4 MPa, about 5 MPa, about 6 MPa, about 7 MPa, about 8 MPa, about 9 MPa, about 10 MPa, about 11 MPa, about 12 MPa, about 13 MPa, about 14 MPa, about 15 MPa, about 16 MPa, about 17 MPa, about 18 MPa, about 19 MPa, about 20 MPa, about 21 MPa, about 22 MPa, about 23 MPa, about 24 MPa, about 25 MPa, about 26 MPa, about 27 MPa, about 28 MPa, about 29 MPa, about 30 MPa, about 31 MPa, about 32 MPa, about 33 MPa, about 34 MPa, about 35 MPa, about 36 MPa, about 37 MPa, about 38 MPa, about 39 MPa, about 40 MPa, about 41 MPa, about 42 MPa, about 43 MPa, about 44 MPa, about 45 MPa, about 46 MPa, about 47 MPa, about 48 MPa, about 49 MPa, or about 50 MPa, inclusive of all values and ranges therebetween.

In an embodiment, the fibrin microthread sutures may have a thread failure load in the range of about 1 mN to about 25 N. For example, the fibrin microthread sutures may have a thread failure load in the range of from about 10 mN to about 20 N, about 10 mN to about 15 N, about 10 mN to about 10 N, about 10 mN to about 5 N, about 10 mN to about 1 N, about 10 mN to about 750 mN, about 10 mN to about 500 mN, about 10 mN to about 400 mN, from about 10 mN to about 375 mN, from 10 mN to about 350 mN, from about 10 mN to about 325 mN, from about 10 mN to about 300 mN, from about 10 mN to about 275 mN, from about 10 mN to about 250 mN, from about 10 mN to about 225 mN, from about 10 mN to about 200 mN, from about 10 mN to about 175 mN, from about 10 mN to about 150 mN, from about 10 mN to about 125 mN, from about 10 mN to about 100 mN, from about 10 mN to about 75 mN, from about 10 mN to about 50 mN, from about 200 mN to about 350 mN, from about 200 mN to about 300 mN, or from about 250 mN to about 350 mN, inclusive of all values and ranges therebetween.

In certain embodiments, the fibrin microthread sutures may have a thread failure load of about 25 N, about 20 N, about 15 N, about 10 N, about 5 N, about 1 N, about 900 mN, about 800 mN, about 700 mN, about 600 mN, about 500 mN, about 400 mN, about 375 mN, about 350 mN, about 325 mN, about 300 mN, about 275 mN, about 250 mN, about 225 mN, about 200 mN, about 175 mN, about 150 mN, about 125 mN, about 100 mN, about 90 mN, about 80 mN, about 70 mN, about 60 mN, about 50 mN, about 40 mN, about 30 mN, about 20 mN, or about 10 mN, inclusive of all values and ranges therebetween.

In an embodiment, the fibrin microthread sutures may have an ultimate load in the range of about 0.1 N to about 20 N. For example, the fibrin microthread sutures may have an ultimate load in the range of from about 0.1 N to about 13 N, from about 0.1 N to about 10 N, from about 0.1 N to about 9 N, from about 0.1 N to about 8 N, from about 0.1 N to about 7.5 N, from about 0.1 N to about 7 N, from about 0.1 N to about 6.5 N, from about 0.1 N to about 6 N, from about 0.1 N to about 5.5 N, from about 0.1 N to about 5 N, from about 0.1 N to about 4.5 N, from about 0.1 N to about 4 N, from about 0.1 N to about 3.5 N, from about 0.1 N to about 3 N, from about 0.1 N to about 2.5 N, from about 0.1 N to about 2 N, from about 0.1 N to about 1.5 N, or from about 0.1 N to about 1 N, inclusive of all values and ranges therebetween.

In certain embodiments, the fibrin microthread sutures may have an ultimate load of about 20 N, about 13 N, about 9 N, about 8 N, about 7.5 N, about 7 N, about 6.5 N, about 6 N, about 5.5 N, about 5 N, about 4.5 N, about 4 N, about 3.5 N, about 3 N, about 2.5 N, about 2 N, about 1.5 N, about 1 N, or about 0.5 N, inclusive of all values and ranges therebetween.

In certain embodiments, the ratio of the stiffness of the fibrin microthread sutures of the invention to the stiffness behavior of a target tissue is about 0.2:1, or about 0.5:1, or about 0.6:1, or about 0.7, or about 0.8:1, or about 0.9:1, or about 1:1, or about 1:1.1, or about 1:1.2, or about 1:1.3, or about 1:1.4, or about 1:1.5, or about 1:2, or about 1:0.5, or about 1:0.6, or about 1:0.7, or about 1:0.8, or about 1:0.9, or about 1.1:1, or about 1.2:1, or about 1.3:1, or about 1.4:1, or about 1.5:1, or about 2:1 or about 5:1.

In certain embodiments, the fibrin microthreads can absorb substantially faster in a target tissue relative to conventional sutures. In some embodiments, the fibrin microthreads described herein can absorb in the target tissue in a substantially shorter amount of time than conventional sutures. In some embodiments, fibrin microthread can be absorbed in the target tissue in the range of about 3 days to about 21 days, for example, 7 days, 8 days, 9 days, 10 days, 11 days, 12 days, 13 days, 14 days, or about 15 days. In a specific embodiment, the fibrin microthreads substantially absorb within a target tissue at the ligature site in about 7 to about 14 days. In some embodiments, the faster absorption of the present fibrin microthread sutures allows for use in treatment methods that require additional medical interventions in a short time. For example, the faster absorption of the present fibrin microthread sutures allow for faster recovery that permits additional medical action that may be required, for instance, further surgeries.

Embodiments of the fibrin microthreads described herein can be configured in any suitable form, shape, or size corresponding to the size and shape of the tissue repair that is desired. The fibrin microthreads may be organized by basic bundling, braiding, twisting, or cabling depending upon specific needs in accordance with textile techniques known to one skilled in the art. For example, in some embodiments a plurality of the fibrin microthreads can be braided or woven together to form a rope or a yarn. In some embodiments, the plurality of the fibrin microthreads can be coupled together to form woven or non-woven meshes, dressing, bandage, gauze, web, film, patch, sheath or graft for application to or implantation in a tissue, for example, for tissue ligation. In various embodiments, the fibrin microthreads can be associated with a substrate (by, for example, coating, wrapping, or otherwise permanently or non-permanently associating the microthreads with the substrate). In certain embodiments, the substrate can be a woven or non-woven mesh, a surgical needle, a surgical pin, a surgical screw, a surgical plate, a patch, a dressing, a bandage, or a natural or mechanical valve.

In various embodiments, the fibrin microthread sutures of the invention comprise filaments of polymerized fibrin that are generally cylindrical in shape. In an embodiment, the fibrin microthread sutures comprise multiple filaments (i.e., multi-filament). The diameter of the filaments is generally in the range of from about 1 µM to about 300 µM. For example, the diameter of the filaments is from about 1 µM to about 290 µM, from about 1 µM to about 280 µM, from about 1 µM to about 270 µM, from about 1 µM to about 260 µM, from about 1 µM to about 250 µM, from about 1 µM to about 240 µM, from about 1 µM to about 230 µM, from about 1 µM to about 220 µM, from about 1 µM to about 210 µM, from about 1 µM to about 200 µM, 1 µM to about 190 µM, from about 1 µM to about 180 µM, from about 1 µM to about 170 µM, from about 1 µM to about 160 µM, from about 1 µM to about 150 µM, from about 1 µM to about 140 µM, from about 1 µM to about 130 µM, from about 1 µM to about 120 µM, from about 1 µM to about 110 µM, from about 1 µM to about 100 µM from about 1 µM to about 90 µM, from about 1 µM to about 80 µM, from about 1 µM to about 70 µM, from about 1 µM to about 60 µM, from about 1 µM to about 50 µM, from about 1 µM to about 40 µM, from about 1 µM to about 30 µM, from about 1 µM to about 20 µM, from about 1 µM to about 10 µM, or from about 1 µM to about 5 µM, inclusive of all values and ranges therebetween. In various embodiments, the diameter of the filaments is about 200 µM, about 190 µM, about 180 µM, about 170 µM, about 160 µM, about 150 µM, about 140 µM, from about 130 µM, about 120 µM, about 110 µM, about 100 µM, about 90 µM, about 80 µM, about 70 µM, about 60 µM, about 50 µM, about 40 µM, about 30 µM, about 20 µM, about 10 µM, or about 5 µM, inclusive of all values and ranges therebetween.

In another embodiment, the fibrin microthread sutures comprise a single filament (i.e., monofilament). Without wishing to be bound by theory, it is believed that monofilament fibrin microthread sutures may reduce the risks for infections. The diameter of the monofilament is generally in the range of from about 100 µM to about 2,000 µM. For example, the diameter of the filaments is from about 100 µM to about 1,900 µM, from about 100 µM to about 1,800 µM, from about 100 µM to about 1,700 µM, from about 100 µM to about 1,600 µM, from about 100 µM to about 1,500 µM, from about 100 µM to about 1,400 µM, from about 100 µM to about 1,300 µM, from about 100 µM to about 1,200 µM, from about 100 µM to about 1,100 µM, from about 100 µM to about 1,000 µM, from about 100 µM to about 900 µM, from about 100 µM to about 800 µM, from about 100 µM to about 700 µM, from about 100 µM to about 600 µM, from about 100 µM to about 500 µM, from about 100 µM to about 400 µM, from about 100 µM to about 300 µM, from about 100 µM to about 200 µM, or from about 100 µM to about 150 µM, inclusive of all values and ranges therebetween. In various embodiments, the diameter of the monofilament is about 2,000 µM, about 1,900 µM, about 1,800 µM, about 1,700 µM, about 1,600 µM, about 1,500 µM, about 1,400 µM, from about 1,300 µM, about 1,200 µM, about 1,100 µM, about 1,000 µM, about 900 µM, about 800 µM, about 700 µM, about 600 µM, about 500 µM, about 400 µM, about 300 µM, about 200 µM, or about 100 µM, inclusive of all values and ranges therebetween.

In some embodiments, the yarns or monofilaments may be further organized into a mesh or "sheet" configuration. These mesh devices can leverage the adjustable stiffness and elasticity of the fibrin yarns or monofilaments and further augment these characteristics through knit or weaving patterns as appropriate. In certain embodiments, the meshes or "sheets" may be useful in support of soft tissue repairs requiring a fast absorbing, mechanically compliant reinforcement or overlay material. In certain embodiments, the device may be useful for retention of delivered materials in a specified tissue or organ by formation of a pouch or patch. In some embodiments, the device may be useful for mechanical reinforcement over larger tissue defects as an overlay which may be sutured or otherwise affixed in place.

In some embodiments, textile engineering techniques are used to generate a three-dimensional weave or mesh. In certain embodiments, the three-dimensional weave or mesh may be used as an organized tissue void filling substrate. Sutured into place at its borders, the three-dimensional weave or mesh can provide initial mechanical support to a tissue defect, prevent abscess formation, and provide organizational cues to ingrowing host cells.

In some embodiments, the yarns can be organized into a reinforcing or isolating sleeve. The sleeve can provide mechanically compliant reinforcement around a healing tissue. The mechanical compliance of the sleeve, particularly used in conjunction with a mechanically compliant suture along with the biocompatibility of fibrin, provides for a minimally inflammatory environment with minimal likelihood for a device-induced adverse outcome such as scar formation, occlusion, or wound breakdown.

In some embodiments, additional filaments of other material types may be integrated into the fibrin yarns or threads as parallel filaments, a core material, or a sheathing. These materials may include, but are not limited to, a range of conventional synthetic or biosynthetic fibers (e.g., polypropylene, nylon, PLGA) and natural fibers (e.g., collagen, silk, elastin). These materials may be added to modulate Young's modulus, UTS, absorption rate, and strength retention profiles. These materials may also be added as yarns integrated into a composite woven or knit device to alter the aforementioned properties in addition to burst mechanics and directional device tensile mechanics. A synthetic fiber can include, but is not limited to, an aliphatic polyester, a poly(amino acid), poly(propylene fumarate), a copoly(etherester), a polyalkylene oxalate, a polyamide, a tyrosine-derived polycarbonate, a poly(iminocarbonate), a polyorthoester, a polyoxaester, a polyamidoester, a polyoxaester containing one or more amine groups, a poly(anhydride), a polyphosphazine, a polyurethane, a biosynthetic polymer, or a combination thereof. The aliphatic polyester can include, but is not limited to, homopolymers or copolymers of lactides; glycolides; ε-caprolactone; hydroxybuterate; hydroxyvalerate; 1,4-dioxepan-2-one; 1,5,8,12-tetraoxyacyclotetradecane-7,14-dione; 1,5-dioxepan-2-one; 6,6-dimethyl-1,4-dioxan-2-one; 2,5-diketomorpholine; p-dioxanone (1,4-dioxan-2-one); trimethylene carbonate(1,3-dioxan-2-one); alkyl derivatives of trimethylene carbonate; δ-valerolactone; β-butyrolactone; γ-butyrolactone, ε-decalactone, pivalolactone, α,α-diethylpropiolactone, ethylene carbonate, ethylene oxalate; 3-methyl-1,4-dioxane-2,5-dione; 3,3-diethyl-1,4-dioxan-2,5-dione; 6,8-dioxabicycloctane-7-one; or combinations thereof. A biosynthetic fiber can include, but is not limited to, a polymer comprising a sequence found in collagen, elastin, thrombin, fibronectin, a starch, gelatin, alginate, pectin, oxidized cellulose, chitin, chitosan, tropoelastin, hyaluronic acid, a ribonucleic acid, a deoxyridonucleic acid, a polypeptide, a polysaccharide, or a combination thereof. A natural fiber can include, but is not limited to, collagen or a collagen-based material, hyaluronic acid or a hyaluronic acid-based material, cellulose or a cellulose-based material, silk and combinations thereof.

In various embodiments, combining the fibrin microthread with a microthread comprising a non-fibrin polymer can include, for example, weaving the fibrin microthread and the microthread comprising the non-fibrin polymer, bundling the fibrin microthread and the microthread comprising the non-fibrin polymer to form a filament, or tying or interlacing the fibrin microthread and the microthread comprising the non-fibrin polymer to form a non-woven mesh. The fibrin microthread and the microthread comprising the non-fibrin polymer can be coextruded. For example, a fibrin microthread can be extruded through one orifice into a receptacle and a non-fibrin microthread can be extruded through a second orifice into the same or a different receptacle.

Examples of apparatus, processes and methods that can be used for forming fibrin microthreads are described in U.S. Patent Publication No. 2011/0034388 and U.S. Pat. No. 8,865,869, the entire disclosures of which are incorporated herein by reference. Additional methods are described herein (e.g. methods for controlling whether the sutures are mono- or multi-filaments).

In certain embodiments, the fibrin microthreads are formed by using a dispensing apparatus, the dispensing apparatus having a first reservoir containing fibrinogen, a second reservoir containing a molecule capable of forming fibrin from the fibrinogen (e.g. thrombin), a blending connector fluidically coupled to the first reservoir and the second reservoir, and a lumen containing device fluidically coupled to the blending connector. A first volume of fibrinogen from the first reservoir is transferred to the blending connector; a second volume of the molecule capable of forming fibrin from the fibrinogen is transferred from the second reservoir to the blending connector; the first volume of fibrinogen and the second volume of the molecule forming a mixture in the blending connector. The mixture from the blending connector is transferred to the lumen containing device in an aqueous bath and the distal end of the lumen containing device is moved through the aqueous bath at a first velocity and the mixture is extruded from the distal end of the lumen containing device into the aqueous bath at a second velocity while moving the distal end of the lumen containing device through the aqueous bath. In some embodiments, the ratio of the second velocity to the first velocity is in the range of about 1.5 to about 6 (e.g. about 1.5, or about 2.0, or about 2.5, or about 3.0, or about 3.5, or about 4.0, or about 4.5, or about 5.0, or about 5.5, or about 6.0). In some embodiments, the mixture is incubated in the aqueous bath for a predetermined incubation time to form the fibrin microthread (e.g. about 1 to about 30 min., or about 5 to about 25 min., or about 10 to about 20 min., or about 15 to about 20 min., or about 1 min., or about 5 min., or about 10 min., or about 15 min., or about 20 min., or about 25 min., or about 30 min.

In certain embodiments, the fibrin microthreads are formed by combining a first volume of fibrinogen with a second volume of a molecule capable of forming fibrin from fibrinogen to form a mixture. The mixture is transferred to a lumen containing device and a distal end of the lumen containing device is disposed in an aqueous bath. The mixture is extruded from the distal end of the lumen containing device while moving the distal end through the aqueous bath. The fibrin microthreads substantially form in the aqueous bath and are then removed from the aqueous bath. As described herein, a plurality of threads formed in this manner are optionally formed into yarns in the bath or outside of the bath after drying.

In an illustrative embodiment, the fibrin microthreads described herein can be formed using a mechanical process. For example, in some embodiments, the fibrin microthreads can be formed by combining fibrinogen and a molecule capable of forming fibrin form the fibrinogen, for example, the enzyme thrombin, to form a mixture. The mixture can be transferred to a lumen containing device, for example, a tube or a conduit. A distal end of the lumen containing device can be disposed in an aqueous bath. The mixture can be extruded from the distal end of the lumen containing device, while moving the distal end of the lumen containing device through the aqueous bath. This deposits the mixture in the aqueous bath that is allowed to form into the fibrin microthread, for example, after incubating for a predetermined time.

Fibrin is a proteolytic cleavage product of fibrinogen. Fibrinogen, a soluble protein typically present in human blood plasma at concentrations between about 2.5 and 3.0 g/L, is intimately involved in a number of physiological processes including homeostasis, angiogenesis, inflammation, and wound healing. Fibrinogen is 340,000 Da hexameric glycoprotein composed of pairs of three different subunit polypeptides, Aα, Bβ, and γ, linked together by a total of 29 disulfide bonds. During the normal course of blood coagulation, the enzyme thrombin cleaves small peptides from the Aα and Bβ chains of fibrinogen to generate the insoluble fibrin monomer. The fibrin monomers self-assemble in a staggered overlapping fashion through non-covalent, electrostatic interactions to form protofibrils; the protofibrils further assemble laterally into thicker fibers that ultimately intertwine to produce a clot.

Fibrinogen is expressed primarily in the liver, although low levels of extrahepatic synthesis have been reported for other tissues, including bone marrow, brain; lung and intestines. The thrombin catalyzed conversion of fibrinogen to fibrin is common to all extant vertebrates and accordingly, the amino acid sequence of fibrinogen is highly conserved evolutionarily. Each polypeptide subunit is the product of a separate but closely linked gene; multiple isoforms and sequence variants have been identified for the subunits. Amino acid sequences for the fibrinogen subunits are in the public domain. The fibrinogen Aα polypeptide is also known as fibrinogen a chain polypeptide; fibrinogen a chain precursor; Fib2; MGC119422; MGC119423; and MGC119425. The fibrinogen Bβ polypeptide is also known as fibrinogen β chain polypeptide; fibrinogen β chain preproprotein; MGC104327; and MGC120405 and the fibrinogen γ polypeptide is also known as fibrinogen γ chain polypeptide and fibrinogen γ chain precursor.

Any form of fibrinogen that retains the ability to function (e.g., retains sufficient activity to form fibrin in the presence of a molecule capable of forming fibrin from fibrinogen) may be used in the manufacture of the fibrin microthreads. The fibrinogen can be a human fibrinogen or a fibrinogen of a non-human primate, a domesticated animal, a bovine tissue, or a rodent. The fibrinogen can be obtained from a naturally occurring source or recombinantly produced. The amino acid sequence of fibrinogen subunit polypeptides can be identical to a standard reference sequence in the public domain. In some embodiments, the fibrinogen can include biologically active variants of a fibrinogen subunit polypeptide. For example, a biologically active variant of a fibrinogen subunit polypeptide can have an amino acid sequence with at least or about 50% sequence identity (e.g., at least or about 50%, about 55%, about 60%, about 65%, about 70%, about 75%, about 80%, about 85%, about 90%, about 95%, about 97%, about 98%, or about 99% sequence identity) to a fibrinogen subunit polypeptide (e.g. one or more of an alpha, beta, and gamma chain). Conservative amino acid substitutions typically include substitutions within the following groups: glycine and alanine; valine, isoleucine, and leucine; aspartic acid and glutamic acid; asparagine, glutamine, serine and threonine; lysine, histidine and arginine;

and phenylalanine and tyrosine. Alternatively, any of the components can contain mutations such as deletions, additions, or substitutions.

The fibrinogen may be partially or substantially pure. The term "substantially pure" with respect to fibrinogen refers to fibrinogen that has been separated from cellular components by which it is naturally accompanied, such that it is at least about 60% (e.g., about 65%, about 70%, about 75%, about 80%, about 85%, about 90%, about 95%, or about 99%), by weight, free from polypeptides and naturally-occurring organic molecules with which it is naturally associated. In general, a substantially pure polypeptide will yield a single major band on a non-reducing polyacrylamide gel. A substantially pure polypeptide provided herein can be obtained by, for example, extraction from a natural source (e.g., blood or blood plasma from human or animal sources), non-human primates (e.g., monkeys, baboons, or chimpanzees), pigs, cows, horses, goats, sheep, dogs, cats, rabbits, guinea pigs, gerbils, hamsters, rats, or mice), chemical synthesis, or by recombinant production in a host cell.

The fibrinogen can include post-translational modifications, i.e., chemical modification of the polypeptide after its synthesis. Chemical modifications can be naturally occurring modifications made in vivo following translation of the mRNA encoding the fibrinogen polypeptide subunits or synthetic modifications made in vitro. The polypeptide can include one or more post-translational modifications, in any combination of naturally occurring, i.e., in vivo, and synthetic modifications made in vitro. Examples of post-translational modifications include glycosylation (e.g., addition of a glycosyl group to asparagine, hydroxy lysine, serine or threonine residues to generate a glycoprotein or glycopeptides). Glycosylation is typically classified based on the amino acid through which the saccharide linkage occurs and can include: N-linked glycosylation to the amide nitrogen of asparagines side chains, O-linked glycosylation to the hydroxyl oxygen of serine and threonine side chains, and C-mannosylation. Other examples of post-translation modification include, but are not limited to, acetylation, for example, the addition of an acetyl group, typically at the N-terminus of a polypeptide; alkylation, for example, the addition of an alkyl group; isoprenylation, for example, the addition of an isoprenoid group; lipoylation, for example, attachment of a lipoate moiety; phosphorylation, for example, addition of a phosphate group to serine, tyrosine, threonine or histidine; methylation, for example, the addition of an methyl group, and biotinylation, for example, acylation of lysine or other reactive amino acid residues with a biotin molecule.

Fibrinogen can be purified using any standard method including, but not limited to, methods based on fibrinogen's low solubility in various solvents, its isoelectric point, fractionation, centrifugation, and chromatograph. Such methods can include, for example, gel filtration, ion exchange chromatography, reverse-phase HPLC, and immunoaffinity purification. partially or substantially purified fibrinogen can also be obtained from commercial sources, including for example Sigma, St. Louis, Mo., Hematologic Technologies, Inc. Essex Junction, Vt., or Aniara Corp. Mason, Ohio.

Any concentration of fibrinogen that results in fibrin microthread formation can be used. For example, in some embodiments, the concentration of fibrinogen can be about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 110 mg/ml, or about 120 mg/ml. In some embodiments, the concentration of fibrinogen can be about 1% Clottable/mL, or about 1.5% Clottable/mL, or about 2% Clottable/mL, or about 2.5% Clottable/mL, or about 3% Clottable/mL, or about 3.5% Clottable/mL, or about 4% Clottable/mL, or about 4.5% Clottable/mL, or about 5% Clottable/mL, or about 7.5% Clottable/mL, or about 10% Clottable/mL.

Fibrinogen can also be produced by recombinant DNA techniques. Nucleic acid segments encoding the fibrinogen polypeptide subunits can be operably linked in a vector that includes the requisite regulatory elements, for example, promoter sequences, transcription initiation sequences, and enhancer sequences, for expression in prokaryotic or eukaryotic cells. Methods well known to those skilled in the art can be used to construct expression vectors containing relevant coding sequences and appropriate transcriptional/translational control signals. Alternatively, suitable vector systems can be purchased from commercial sources. The nucleic acid molecules can be synthesized (e.g., by phosphoramidite based synthesis) or obtained from a biological cell, such as the cell of a mammal. The nucleic acids can be those of mammal, for example, humans, a non-human primates, cattle, horses, pigs, sheep, goats, dogs, cats, rabbits, guinea pigs, hamsters, rats, or mice.

The molecule capable of forming fibrin from fibrinogen can be any naturally occurring or synthetic molecule capable of cleaving fibrinogen, thereby producing fibrin. For example, in some embodiments, the molecule can include thrombin. The aqueous bath can include any aqueous medium that is compatible with the activity of the fibrin-forming enzyme for example, thrombin. Suitable aqueous mediums can include buffer systems such as, for example, HEPES-buffered saline, tris-buffered saline, phosphate buffered saline, MES, PIPES. The buffer may also include a divalent cation such as, for example, $CaCl_2$ (e.g. about 1 mM, or about 3 mM, or about 5 mM, or about 7.5 mM, or about 10 mM, or about 12.5 mM, or about 15 mm, or about 17.5 mM, or about 20 mM, or about 25 mM, or about 30 mM). In an illustrative embodiment, the aqueous bath comprises about 10 mM HEPES and about 20 mM $CaCl_2$. Any concentration of thrombin that results in fibrin microthread formation can be used such as, for example, about 4 U/ml, about 6 U/ml, about 7 U/ml, about 8 U/ml, about 9 U/ml, about 10 U/ml, about 12 U/ml, about 14 U/ml, about 16 U/ml, about 18 U/ml, about 20 U/ml, about 30 U/ml, about 40 U/ml, about 50 U/ml, about 60 U/ml, about 70 U/ml, about 80 U/ml, about 90 U/ml, or about 100 U/ml. Any of the concentrations of fibrinogen, the molecule capable of forming fibrin from fibrinogen, the pH of the aqueous medium, and the swelling temperature may be adjusted to improve fibrin microthread formation. For example, fibrinogen from different sources, for example, different mammalian species or different isoforms of fibrinogen from the same species, may require different cleavage conditions in order to synthesize fibrin microthreads of requisite mechanical or tissue regeneration properties.

In some embodiments, the mixture of fibrinogen and molecule capable of forming fibrin from fibrinogen can be incubated in the aqueous bath for a predetermined incubation time to allow fibrin to substantially form in the aqueous bath. For example, the mixture can be incubated for at least about 1 minute, about 2 minutes, about 3 minutes, about 5 minutes, about 10 minutes, about 15 minutes, about 20 minutes, about 25 minutes, about 30 minutes, about 40 minutes, about 45 minutes, about 50 minutes, about 55 minutes, about 1 hour, about 2 hours, about 3 hours, about 4 hours, about 5 hours, or even more.

The fibrin microthreads can be recovered from the aqueous bath and dried. The fibrin microthreads can be dried in air, or any other gas, for example, nitrogen. The drying temperature may be ambient temperature, for example, about 25 degrees Celsius, or a temperature that is mildly elevated relative to ambient temperature, for example, in the range of about 28 degrees Celsius to about 44 degrees Celsius (e.g., about 29, about 30, about 31, about 32, about 33, about 34, about 35, about 36, about 37, about 38, about 39, about 40, about 41, about 42, or about 43 degrees Celsius inclusive of all ranges therebetween).

In some embodiments, the fibrin microthreads can be submitted to one or more treatments to diminish any bioburden. These treatments can be configured to inactivate or kill substantially all microorganisms (e.g., bacteria, fungi (including yeasts), and/or viruses) in the fibrin microthreads. In various embodiments, the treatments can be used to sterilize the fibrin microthreads. Suitable sterilization treatments can include ultra-violet light, autoclave, ethylene oxide, gamma radiation, electron beam radiation, supercritical carbon dioxide sterilization, any other sterilization treatment process or combination thereof.

The fibrin microthreads described herein can be hydrated before performing wound ligation. Hydration can be performed in any suitable aqueous medium, for example, a buffer solution such as, for example, phosphate buffered saline, HEPES-buffered saline, tris-buffered saline, MES, PIPES, Lactated Ringer's solution, Dulbecco's minimum essential media (DMEM), Ham's F-10 media, Ham's F-12 media, minimum essential media (MEM), any other suitable aqueous solution or combination thereof. The hydration can swell the fibrin microthreads.

Methods of Producing Fibrin Microthread Sutures

In various embodiments, methods for producing fibrin microthreads are provided. In an embodiment, methods for producing multifilament fibrin microthreads are provided. The method comprises an extrusion step in which the microthreads are extruded into a bath (e.g., aqueous buffer bath), followed by drying the individual microthreads. Varying numbers of dried threads can then be twisted together to produce a multifilament microthread yarn.

In an alternative embodiment, methods for producing monofilament fibrin microthreads are provided. The method comprises an extrusion step in which the microthreads are extruded into a bath as described herein. Prior to removal from the extrusion bath, varying numbers of microthreads (e.g. more than 2, more than 5, more than 6, more than 7, more than 8, more than 9, or more than 10 such as 3, 4, 5, 6, 7, 8, 9, 10, 11, 12, 13, 14, or 15) are pulled together in the bath (e.g. buffer solution) to form a single, cohesive thread. The thread is then removed from the bath and allowed to dry.

In certain embodiments, multiple layers of fibrin are deposited into the bath to form multifilament or monofilament microthreads. For example, about 1 layer, 2 layers, 3 layers, 4 layers, 5 layers, 6 layers, 7 layers, 8 layers, 9 layers, 10 layers, 11 layers, 12 layers, 13 layers, 14 layers, 15 layers, 16 layers, 17 layers, 18 layers, 19 layers, or 20 layers may be deposited into the bath to form multifilament or monofilament fibrin microthreads. In an embodiment, monofilament fibrin microtheads are formed.

In various embodiments, the time between each layer deposition is from about 1 second to about 10 minutes. For example, the time between each layer deposition is from about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 70 seconds, about 80 seconds, about 90 seconds, about 100 seconds, about 110 seconds, about 120 seconds, about 150 seconds, about 3 minutes, about 4 minutes, about 5 minutes, about 6 minutes, about 7 minutes, about 8 minutes, about 9 minutes, or about 10 minutes.

In various embodiments, thrombin is used for forming fibrin microthreads. The thrombin concentration may be in the range of about 1 U/mL to about 100 U/mL, about 1 U/mL to about 95 U/mL, about 1 U/mL to about 90 U/mL, about 1 U/mL to about 85 U/mL, about 1 U/mL to about 80 U/mL, about 1 U/mL to about 75 U/mL, about 1 U/mL to about 70 U/mL, about 1 U/mL to about 65 U/mL, about 1 U/mL to about 60 U/mL, about 1 U/mL to about 55 U/mL, about 1 U/mL to about 60 U/mL, about 1 U/mL to about 55 U/mL, about 1 U/mL to about 50 U/mL, about 1 U/mL to about 45 U/mL, about 1 U/mL to about 40 U/mL, about 1 U/mL to about 35 U/mL, about 1 U/mL to about 30 U/mL, about 1 U/mL to about 25 U/mL, about 1 U/mL to about 20 U/mL, about 1 U/mL to about 15 U/mL, about 1 U/mL to about 10 U/mL, about 1 U/mL to about 9 U/mL, about 1 U/mL to about 8 U/mL, about 1 U/mL to about 7 U/mL, about 1 U/mL to about 6 U/mL, about 1 U/mL to about 5 U/mL, about 1 U/mL to about 4 U/mL, about 1 U/mL to about 3 U/mL, or about 1 U/mL to about 2 U/mL. For example, the thrombin concentration may be about 1 U/mL, about 2 U/mL, about 3 U/mL, about 4 U/mL, about 5 U/mL, about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL. about 25 U/mL, about 30 U/mL, about 35 U/mL, about 40 U/mL, about 45 U/mL, about 50 U/mL, about 55 U/mL, or about 60 U/mL, inclusive of all values and ranges therebetween.

In various embodiments, $CaCl_2$ is included in the bath used for extrusion. The $CaCl_2$ concentration may be in the range of about 0.1 mM to about 20 mM, about 0.1 mM to about 15 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, or about 0.1 mM to about 1 mM. For example, the $CaCl_2$ concentration may be about 0.1 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM, inclusive of all values and ranges therebetween.

In various embodiments, an additional step of rehydrating and stretching the fibrin microthreads is included. In such embodiments, the fibrin microthreads are extruded into a bath where they are maintained at 100% of their initial length and allowed to dry. Subsequently, the fibrin microthreads are rehydrated in, for example, distilled water, and stretched to at least about 110%, about 120%, about 130%, about 140%, about 150%, about 160%, about 170%, about 180%, about 190%, about 200%, about 250%, about 300%, about 400%, or about 500% of their initial length. The stretched fibrin microthreads are then allowed to dry. It is believed that such an additional drying, rehydrating, and stretching step may enhance the mechanical strength of the fibrin microthread.

Alternatively, the fibrin microthreads are stretched directly after extrusion. For example, the fibrin microthreads are stretched in bath directly after extrusion. In such embodiments, the fibrin microthreads are stretched within about 60 minutes of initial extrusion. For example, the fibrin microthreads are stretched within about 60 minutes, about 55 minutes, about 50 minutes, about 45 minutes, about 40 minutes, about 35 minutes, about 30 minutes, about 25 minutes, about 20 minutes, about 15 minutes, about 10 minutes, about 9 minutes, about 8 minutes, about 7 minutes, about 6 minutes, about 5 minutes, about 4 minutes, about 3 minutes, about 2 minutes, or about 1 minute of initial extrusion.

In certain embodiments, the fibrin microthreads (for example, multifilament or monofilament fibrin microthreads) are twisted following stretching. In an embodiment, the stretching improves cross-sectional uniformity. In various embodiments, twisting may be performed at a level of between 0.1 twists/cm to around 3 twists/cm. For example, twisting may be performed at 0.1 twists/cm, 0.5 twists/cm, 1 twists/cm, 1.5 twists/cm, 2 twists/cm, 2.5 twists/cm, or 3 twists/cm.

To form sutures using either the multifilament or monofilament fibrin microthreads, dried threads are inserted into the bore hold of a standard drilled-end surgical needle and crimped into place. In various embodiments, the sutures are readily attached to needles of various types as described herein (for example, bored-end needle or eyelet-style needle). Optionally, the sutures are packaged and sterilized, for example, via a 12-hour ethylene oxide cycle. In some embodiments, the needle is a straight, ¼ circle, ⅜ circle, ½ circle (e.g. CT, CT-1, CT-2 and CT-3), ⅝ circle, compound curved, half curved (ski), half curved at both ends (canoe), taper, cutting, reverse cutting, trocar point, blunt point, or a side cutting needle. By way of illustration ETHICON needles (NOVARTIS), LOOK needles (SURGICAL SPECIALTIES), or SYNETURE needles (COVIDIEN) may be used in the present invention.

In certain embodiments, the fibrin microthreads (for example, multifilament or monofilament fibrin microthreads) are twisted following needle attachment. In various embodiments, twisting may be performed at a level of between 0.1 twists/cm to around 3 twists/cm. For example, twisting may be performed at 0.1 twists/cm, 0.5 twists/cm, 1 twists/cm, 1.5 twists/cm, 2 twists/cm, 2.5 twists/cm, or 3 twists/cm.

Additional Therapeutic Agents and Combination Therapy

In some embodiments, one or more therapeutic agents can be incorporated in the fibrin microthreads. The therapeutic agent can include, for example, a growth factor, a protein, a chemotherapeutic agent, a vitamin, a mineral, an antimicrobial agent, a small organic molecule, or a biological cell. The therapeutic agent can be incorporated in the fibrin microthread using any suitable process such as, for example, covalent bonding to the fibrin microthread, surface adsorption, or physical incorporation during the mixing of the fibrinogen and the molecule capable of forming fibrinogen, or absorption during the hydration process.

In some embodiments, the therapeutic agents can include agents that promote tissue regeneration. In such embodiments, the therapeutic agents can include growth factors including, for example, cytokines and interleukins, extracellular matrix proteins and/or biologically active fragments thereof (e.g., RGD-containing peptides), blood and serum proteins, nucleic acids, hormones, vitamins, chemotherapeutics, antibiotics and cells. These agents can be incorporated into the fibrin microthreads prior to implantation in a host tissue. Alternatively, the therapeutic agents can be injected into or applied to fibrin microthreads already implanted in the host tissue. These agents can be administered singly or in combination. For example, the fibrin microthreads can be used to deliver cells, growth factors and small molecule therapeutics concurrently, or to deliver cells plus growth factors, or cells plus small molecule therapeutics, or growth factors plus small molecule therapeutics.

Growth factors that can be incorporated into the fibrin microthreads can include any of a wide range of cell growth factors, angiogenic factors, differentiation factors, cytokines, hormones, and chemokines known in the art. Growth factors can be polypeptides that include the entire amino acid sequence of a growth factor, a peptide that corresponds to only a segment of the amino acid sequence of the native growth factor, or a peptide that is derived from the native sequence that retains the bioactive properties of the native growth factor. The growth factor can be a cytokine or interleukin. Any combination of two or more of the growth factors can be included in the fibrin microthreads. Examples of relevant factors include vascular endothelial cell growth factors (VEGF) (e.g., VEGF A, B, C, D, and E), platelet-derived growth factor (PDGF), insulin-like growth factor (IGF) I and IGF-II, interferons (IFN) (e.g., IFN-α, β or γ), fibroblast growth factors (FGF) (e.g., FGF 1, FGF-2, FGF-3, FGF-4-FGF-10), epidermal growth factor, keratinocyte growth factor, transforming growth factors (TGF) (e.g., TGFα or β), tumor necrosis factor-a, an interleukin (IL) (e.g., IL-I, IL-2, Il-17-IL-18), Osterix, Hedgehogs (e.g., sonic or desert), SOX9, bone morphogenetic proteins (BMPs), in particular, BMP 2, 4, 6, and (BMP-7 is also called OP-1), parathyroid hormone, calcitonin prostaglandins, or ascorbic acid.

In some embodiments, the therapeutic agents can include proteins. In some embodiments, the proteins can be delivered to the host tissue by including in the fibrin microthreads any one of the following: (a) expression vectors (e.g., plasmids or viral vectors) containing nucleic acid sequences encoding any one or more of the above factors that are proteins; or (b) cells that have been transfected or transduced (stably or transiently) with such expression vectors. Such transfected or transduced cells will preferably be derived from, or histocompatible with, the host tissue. However, it is possible that only short exposure to the factor is required and thus histo-incompatible cells can also be used. Other useful proteins can include, without limitation, hormones, extracellular antibodies, extracellular matrix proteins, and/or biologically active fragments thereof (e.g., RGD-containing peptides) or other blood and serum proteins, e.g., fibronectin, albumin, thrombospondin, Von Willebrand factor and fibulin.

In some embodiments, the therapeutic agents can include small molecule drugs, thus facilitating localized drug delivery. Long-term systemic administration of antibiotics may only be partially effective against subclinical infections. Incorporation of antimicrobial agents into the fibrin microthreads can provide local high concentrations of antibiotics, thus minimizing the risk of adverse effects associated with long term high systemic doses. Examples of antibiotics include, without limitation, any representative classes of antibiotics, e.g., 1) aminoglycosides, such as gentamycin, kanamycin, neomycin, streptomycin or tobramycin; 2) cephalosporins, such as cefaclor, cefadroxil or cefotaxime; 3) macrolides, such as azithromycin, clarithromycin, or erythromycin; 4) penicillins, such as amoxicillin, carbenicillin or penicillin; 5) peptides, such as bacitracin, polymixin B or vancomycin; 6) quinolones, such as ciprofloxacin, levofloxacin, or enoxacin; 7) sulfonamides, such as sulfamethazole, sulfacetimide; or sulfamethoxazole; 8) tetracyclines, such as doxycycline, minocycline or tetracycline; 8) other antibiotics with diverse mechanisms of action such as rifampin, chloramphenicol, or nitrofuratoin. Other antimicrobial agents, e.g., antifungal agents and antiviral agents can also be used.

In some embodiments, the therapeutic agents can include anti-inflammatory agents. In some embodiments, the anti-inflammatory agents can include, non-steroidal anti-inflammatory drugs (NSAIDs) such as, for example, aspirin, choline and magnesium salicylates, celecoxib, diclofenac potassium, diclofenac sodium, diclofenac sodium with misoprostol, diflunisal, etodolac, fenoprofen, flurbiprofen, ibuprofen, indomethacin, ketoprofen, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, any other suitable NSAID or a combination thereof. In some embodiments, the anti-inflammatory agents can include corticosteroids such as, for example, hydrocortisone, hydrocortisone acetate, cortisone acetate, tixocortol pivalate, prednisolone, methylprednisolone, methylprednisolone aceponate, prednisone, triamcinolone acetonide, triamcinolone alcohol, mometasone, mometasone furoate, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, hydrocortisone valerate, flurandrenolide, triamcinolone acetonide, ciclesonide, halobetasol, diflorasone diacetate, fluocinonide, halicinonide, amcinonide, desoximetasone, fluticasone propionate, betamethasone dipropionate, desonide, alclometasone dipropionate, clobetasol propionate, prednicarbate, any other suitable corticosteroid or a combination thereof.

In some embodiments, the therapeutic agents can include cells, for examples stem cells. For example, histocompatible, viable cells can be included in the fibrin microthreads to produce a permanently accepted graft that may be remodeled by the host tissue. Cells can be derived from the intended recipient or an allogeneic donor. Cell types with which the fibrin microthreads can be repopulated include, but are not limited to, embryonic stem cells (ESC), adult or embryonic mesenchymal stem cells (MSC), monocytes, hematopoetic stem cells, gingival epithelial cells, endothelial cells, fibroblasts, or periodontal ligament stem cells, prochondroblasts, chondroblasts, chondrocytes, pro-osteoblasts, osteocytes, or osteoclast. Any combination of two or more of these cell types (e.g., two, three, four, five, six, seven, eight, nine, or ten) may be used to repopulate the biocompatible tissue repair composition. Methods for isolating specific cell types are well known in the art. Donor cells may be used directly after harvest or they can be cultured in vitro using standard tissue culture techniques. Donor cells can be infused or included in the fibrin microthreads in situ just prior to placing of the biocompatible tissue repair composition in a mammalian subject. Donor cells can also be co-cultured with the fibrin microthreads using standard tissue culture methods known to those in the art.

Methods of Treatment

The fibrin microthread sutures of the present invention approximate the mechanical properties of the target tissue in which the sutures are implanted. In various embodiments, the fibrin microthread sutures are less stiff and more elastic than conventional sutures. Without wishing to be bound by theory, it is believed that the sutures of the invention, which are able to flex, bend, and stretch with, for example, a wound, can minimize the burden placed upon local tissue to accommodate mechanical displacement, this burden instead being shared with the suture. This decreases the extent of stress localization in the tissue where the suture is anchored as well as reduces damage to the cells immediately surrounding the sutures, thereby preventing or reducing collagen deposition, fibrosis, scarring, inflammation, and/or cell death. Mitigation of these factors also results in decreased incidence of suture extrusion, hypertrophic scar formation, keloid formation, wound dehiscence, incisional hernia, and in the case of tubular tissues, occlusion.

Further still, the fibrin microthread sutures of the present invention can be adapted for use at a repair site with varying levels of hypertrophy or swelling. The ability of the sutures to have a degree of elasticity allows initial closure to be made in a swollen tissue (for example, during and immediately after operation) and maintain tissue approximation post-hypertrophy through suture contraction. As such, the increased elasticity and decreased stiffness of the inventive suture place a lesser initial tensile load on the tissue by stretching the suture during initial repair to account for maintenance of tension following tissue shrinkage post-operation.

In various embodiments, the fibrin microthread sutures of the present invention promotes wound closure or healing by preventing or reducing excess collagen deposition at the ligation site leading to little or no fibrosis or scarring. In various embodiments, the fibrin microthread sutures of the invention prevent or reduce persistent hypercellularity and/or inflammation at a target tissue. In various embodiments, the fibrin microthread sutures of the invention prevent or reduce cell death at a target tissue.

Scarring as a byproduct of fibrosis as well as inflammation are of particular concern in topical wound ligatures and ligatures performed during aesthetic surgery. For example, approximately 1.7 million aesthetic surgery procedures are performed every year in the United States alone. It is desirable in aesthetic surgery procedures and other high sensitivity or high visibility tissue ligation applications such as sensitive facial tissue surgical procedures, that the ligation sutures produce minimal scarring and inflammation in the host tissue. Additional surgeries such as peripheral nerve surgery and detached retina surgery would also benefit substantially from a minimally inflammatory suture.

Normal wound healing follows a well-regulated course, and conceptually consists of three distinct stages. The first stage, the inflammatory stage, is intensely degradative. It begins immediately after injury and provides a means to remove damaged tissues and foreign matter from the wound. A few days after injury, the second stage, the proliferation and matrix synthesis stage, begins. During this stage, fibroblasts from surrounding tissues move into the wound and proliferate. The fibroblasts actively produce collagen, which they secrete into the extracellular matrix. Newly synthesized collagen forms cross-linked fibrils, which provide structural integrity to the wound. After several weeks, the final stage, the remodeling stage, begins. During the remodeling stage, the collagen fibrils, which previously were randomly oriented, align in the direction of mechanical tension, providing further mechanical strength to the wound. The repair process is completed when the skin regains its chemical and physical barrier functions.

Excessive scarring results from an imbalance in the anabolic and catabolic wound healing process. In the formation of an excessive scar, more collagen is produced than is degraded. As a result, the scar grows larger than is required for wound healing, with an over-production of cells, collagen, and proteoglycan. Keloid scars, or keloids, are overgrowths of dense fibrous tissue that result from variations in normal wound healing. The dense fibrous tissue of a keloid extends beyond the borders of the original wound, and usually does not regress spontaneously. Thus, keloid scarring is out of proportion to the severity of the inciting wound. Likewise, hypertrophic scars also are overgrowths of dense fibrous tissue that result from abnormal wound healing. However, hypertrophic scars do not extend beyond the original boundaries of a wound. Also unlike keloids, hypertrophic scars reach a certain size, then stabilize or regress. By preventing or reducing excess collagen deposition at the ligation site, methods of the invention prevent or reduce scarring at the target tissue. In some embodiments, methods of the invention improve the cosmetic appearance of scars at a target tissue. In various embodiments, the methods of the invention prevent or reduce keloid formation. In other embodiments, the methods of the invention prevent or reduce hypertrophic scar formation.

The amount of fibrosis or scarring (e.g., collagen deposition) in a host tissue, for example, after healing of an incision wound, a suture, or any other physical injury healing can be determined using visual methods. Examples of visual methods used for measuring the extent of scarring include: (a) the Vancouver scar scale (VSS) that ranges from 0-13 and quantifies scars on the basis of vascularity, height/thickness, pliability, and pigmentation; (b) the visual analog scale (VAS) that ranges from 0 (excellent) to 100 (poor) and quantifies scars on the basis of vascularity, pigmentation, acceptability, observer comfort plus contour and summing the individual scores; (c) the patient and observer scale which ranges from 5-50 and quantifies scars on the basis of VSS plus surface area; patient assessments of pain, itching, color, stiffness, thickness, relief; (d) the Manchester scar scale which ranges from 5 (best) to 18 (worse) and quantifies scars on the basis of VAS plus scar color, skin texture, relationship to surrounding skin, texture, margins, size, multiplicity; and (e) the Stony Brook scar scale which ranges from 0 (worst) to 5 (best) and quantifies scars on the basis of VAS plus width, height, color, presence of suture/staple marks. Fibrosis or scarring can also be quantified in terms of collagen deposition by performing histology analysis, for example, analysis of histology samples stained with any suitable dyes or stains described herein (including as disclosed by Ross and Pawlina (2006), *Histology: A Text and Atlas*, Hagerstown, Md.: Lippincott Williams and Wilkins) and using the histological activity index (HAI) scale described herein.

In some embodiments, the fibrin microthread sutures can elicit substantially reduced scarring relative to conventional sutures (by way of non-limiting example, when used in aesthetic surgery). In various embodiments, the present sutures provide for reduced scarring assessed by one or more of the VSS (e.g. lower scores, such as about 0, or about 1, or about 2, or about 3), the VAS (e.g. lower scores, such as about 0, or less than about 5, or less than about 10, or less than about 15, or less than about 20, or less than about 25), the patient and observer scale (e.g., lower scores, such as about 5, or about 6, or about 7, or about 8, or about 9, or about 10), Manchester scar scale (e.g. lower scores, such as about 5, or about, 6, or about 7, or about 8, or about 9), and the Stony Brook scar scale (e.g. higher scores, such as about 3, or about 4, or about 5). In some embodiments, the fibrin microthread sutures can elicit substantially reduced collagen deposition relative to conventional sutures and thereby, result in reduced scarring at the wound site. In some embodiments, the fibrin microthread sutures can have a histopathological score of collagen deposition of less than about 1.5 (e.g., about 7 days, or 14 days after implantation in a host tissue), for example, about 1.4, about 1.3 about 1.2, about 1.1, about 1, about 0.5, or about 0 (e.g., about 7 days, or 14 days after implantation in a host tissue). In a specific embodiment, the fibrin microthread sutures have a histopathological score of collagen deposition at the ligature site of less than about 1.3 (e.g., about 7 days, or 14 days after implantation in a host tissue).

In various embodiments, the fibrin microthread sutures of the invention prevent or reduce persistent hypercellularity and/or inflammation at a target tissue. For example, the fibrin microthread sutures of the invention may prevent or reduce infiltration or recruitment of inflammatory cells and/or proliferation of endothelial and mesangial cells at the target tissue where the sutures are anchored, thus preventing or reducing inflammation at the target tissue.

Inflammation can be measured in various ways. Chronic inflammation can be measured using the erythrocyte sedimentation rate (ESR) test. The ESR test is a non-specific test in which a blood sample from a host (e.g., a patient) is disposed in a container, for example, a vial or a tube and maintained in the vial or tube for about an hour or more. The amount of red blood cells that settle to the bottom of the container in 1 hour is used as a non-specific marker in determining the level of inflammation in the host. Enzyme linked immunosorbent assay (ELISA) can also be used to determine the concentration of inflammation biomarkers (e.g., cytokines, C-reactive protein, interleukin-6, or any other inflammation biomarkers) in a blood or plasma sample and determine inflammation in the host. Coulter counters can also be used to count the number of white blood cells, neutrophils, eosinophils, macrophages, lymphocytes, leukocytes, granulocytes, or any other immune cell included in the host immune response that can cause inflammation.

Inflammation can also be assessed using histological techniques, as are known in the arts (see e.g., Ross and Pawlina (2006). *Histology: A Text and Atlas*. Hagerstown, Md.: Lippincott Williams and Wilkins, the contents of which are hereby incorporated by reference herein in their entirety). For example, hematoxylin and eosin (H&E or HE) may be used with, for example, light microscopy. Hematoxylin, a basic dye, stains nuclei blue because of its affinity for nucleic acids in the cell nucleus. Eosin, an acidic dye, stains the cytoplasm pink. Trichrome is another common staining method that includes three colored dyes that can be formulated to stain erythrocytes orange (or yellow), muscle red and collagen blue. Red dyes that can be used in the trichrome stain include without limitation acid fuchsin, xylidine ponceau, chromotrope 2R, biebrich scarlet, ponceau 6R, and phloxine. Blue dyes that can be used in the trichrome stain include without limitation aniline blue, methyl blue, and water blue. Yellow dyes that can be used in the trichrome stain include without limitation picric acid, orange G, martius yellow, tartrazine, and milling yellow.

Uranyl acetate and lead citrate may be used to impart contrast to tissue in, for example, the electron microscope. Furthermore, any one of the following illustrative stains may be used: Toluidine blue, Masson's trichrome stain, Weigert's elastic stain, Heidenhain's AZAN trichrome stain, silver stain, Wright's stain, Orcein stain, periodic acid-Schiff (PAS) stain, any other suitable stain or combination thereof. Such stains are interpreted as common in histological analysis (including as disclosed by Ross and Pawlina (2006), *Histology: A Text and Atlas*, Hagerstown, Md.: Lippincott Williams and Wilkins).

The level of acute inflammation, for example, inflammation of the host tissue due to an incision wound, a suture, or a physical injury, can also be measured using histopathological scoring of histology samples, for example, histology samples stained with any of the stains or dyes described herein. The inflammation in the histopathological stains is quantified using a semi-quantitative scale called the histological activity index (HAI). The scale ranges from a minimum inflammation activity score of 0 to a maximum score of 3, where: 0=No inflammatory activity/None (no infiltration of the epithelium by neutrophils); 1=Mildly active/Trace (Neutrophil infiltration of<50% of sampled crypts or cross sections, no ulcers or erosions); 2=Moderately active/Apparent (Neutrophil infiltration of 50% of sampled crypts or cross sections, no ulcers or erosions); and 3=severely active/Prominent (Erosion or ulceration, irrespective of other features).

In some embodiments, the fibrin microthread sutures described herein can be used in various surgical procedures or suture techniques such as, for example, ligating open wounds or incisions such that the inflammation elicited in the host tissue due to implantation of the fibrin microthread sutures (by way of non-limiting example, when used in plastic surgery) is substantially less than inflammation caused by conventional sutures. In some embodiments, the fibrin microthread sutures can have a histopathological score of overall inflammation in the host tissue of less than about 1.5 such as, for example, about 1.4, or about 1.3, or about 1.2, or about 1.1, or about 1.0, or about 0.9, or about 0.8, or about 0.7, or about 0.6, or about 0.5, or about 0.4, or about 0.3, or about 0.2, or about 0.1, or even 0. In a specific embodiment, the fibrin microthread sutures have a histopathological score of overall inflammation at the ligature site of less than about 1.3.

In various embodiments, the present fibrin microthread sutures prevent or reduce inflammation at the suture site as characterized by an absence or reduction in one or more of edema, erythema, tenderness, induration, discharge, and nodule formation relative to suturing with conventional materials. In other embodiments, the present fibrin microthread sutures prevent or reduce pruritus and/or numbness at the target tissue.

In further embodiments, the present fibrin microthread sutures prevent or reduce cell death at the suture site. It is believed that by minimizing stress localization, the inventive fibrin microthread sutures prevents or minimizes the extent of cell death and tissue damage at the target tissue where the sutures are anchored. In an embodiment, the inventive fibrin microthread sutures prevent or reduce apoptosis at the target tissue. In another embodiment, the inventive fibrin microthread sutures prevent or reduce necrosis at the target tissue. Methods for measuring cell apoptosis or necrosis are established in the art.

In yet further embodiments, the present fibrin microthread sutures prevent or reduce infection at the suture site. In a particular embodiment, fibrin microthread sutures derived from monofilament fibrin microthreads significantly reduce infection at the suture site.

Embodiments of the fibrin microthread sutures described herein can be used for promoting the closure and healing of wounds. In certain embodiments, the wounds are associated with a surgical wound. In other embodiments, the wounds are associated with trauma.

The fibrin microthread sutures described herein can be used for performing any desired surgical procedure. In an embodiment, the fibrin microthread sutures described herein may be used for a surgical procedure involving skin grafting. In other embodiments, the fibrin microthread sutures can be used to perform aesthetic or cosmetic surgical procedures. For example, in some embodiments the fibrin microthread sutures can be used as sutures in a facial plastic surgery procedure including, but not limited to blepharoplasty, rhinoplasty, rhytidectomy, genioplasty, facial implants, otoplasty, hair implantation, cleft lip and cleft palate repair. In some embodiments, the fibrin microthread sutures can be used as sutures in a body plastic surgery procedure including but not limited to abdominoplasty, brachioplasty, thigh lift, breast reduction, breast augmentation, body contouring, liposuction, hand surgery, any other aesthetic or cosmetic surgery procedure or combination thereof. In such embodiments, the fibrin microthread sutures can be used in place of conventional sutures such that there is substantially reduced inflammation and scarring of the target tissue after the surgical procedure. Thus, use of fibrin microthread sutures in plastic and cosmetic surgery procedures can lead to faster recovery and substantially no visible signs of the incision wounds formed during the surgical procedure.

In some embodiments, the fibrin microthread sutures described herein can be used as sutures in any one of a cardiac surgery, skeletal muscle repair, congenital or incision hernia repair, abdominal surgery, laproscopic incision closure, organ prolapse surgery, gastrointestinal surgery, neurosurgery, severed limb reattachment surgery, open heart surgery, orthopedic surgery, blepharoplasty, rhinoplasty, otoplasty, rhytidectomy, aesthetic surgery, skin closure, and any other surgical procedure or combination thereof. In any such embodiments, the fibrin microthread sutures described herein can provide, for example, substantially reduced inflammation, little or no scarring at the host tissue, and fast and extensive adsorption into the host tissue within about 7-14 days.

The fibrin microthread sutures described herein can be used to ligate or repair soft tissue such as, for example, skin, tendon, ligament, fascia, fibrous tissue, fat, synovial membrane, and muscle, nerve and blood vessel. In certain embodiments, the fibrin microthread sutures can be used to ligate or repair simple squamous epithelia, stratified squamous epithelia, cuboidal epithelia, or columnar epithelia, connective tissue (e.g., loose connective tissue, also known as areolar connective tissue), fibrous connective tissue (e.g., tendons, which attach muscles to bone, and ligaments, which joint bones together at the joints), and muscle tissue (e.g., skeletal muscle, which is responsible for voluntary movements; smooth muscle, which is found in the walls of the digestive tract, bladder arteries and other internal organs; and cardiac muscle, which forms the contractile wall of the heart). The fibrin microthread sutures can be used to repair soft tissues in many different organ systems that fulfill a range of physiological functions in the body. These organ systems can include, but are not limited to, the muscular system, the genitourinary system, the gastroenterological system, the integumentary system, the circulatory system and the respiratory system. In an embodiment, the fibrin microthread sutures are useful for ligating or repairing a target tissue such as the skin. In other embodiments, the fibrin microthread sutures are useful for ligating or repairing, for example, blood vessels, ureters, peripheral nerves, portions of the eye, mucous membranes. In certain embodiments, the fibrin microthread sutures are useful for ligating or repairing a target tissue that is hypertrophic or swollen. In other embodiments, the fibrin microthread sutures are useful for ligating or repairing target tissues or organs which may suffer function loss through occlusion caused by scarring.

Methods of delivering fibrin microthreads to a ligation site for repairing or ameliorating damaged or defective tissue are described in, for example, U.S. Patent Publication No. 2011/0034867, the entire disclosures of which are incorporated herein by reference.

The present fibrin microthread sutures find use in a variety of suture techniques, including but not limited to, the simple interrupted stitch, the vertical and horizontal mattress stitch, the running or continuous stitch, the chest drain stitch, the corner stitch, the purse-string suture, the FIG. 8 stitch, and the subcuticular stitch.

In various embodiments, the fibrin microthread sutures of the invention can be used in combination with other therapeutic agents and/or therapeutic regimens.

In an embodiment, the present fibrin microthread sutures may be used in combination with topical cyanoacrylate adhesives ("liquid stitches"), a.k.a. medicinal grade super glue in wound closure. Cyanoacrylate is the generic name for cyanoacrylate based fast-acting glues such as methyl-2-cyanoacrylate, ethyl-2-cyanoacrylate (commonly sold under trade names like SUPERGLUE and KRAZY GLUE) and n-butyl-cyanoacrylate. Skin glues like INDERMIL and HISTOACRYL, composed of n-butyl cyanoacrylate, are also useful. Further, 2-octyl cyanoacrylate (e.g. LIQUIBAND, SURGISEAL, FLORASEAL, and DERMABOND) may be used.

In another embodiment, the present fibrin microthread sutures may be used in combination with various skin closure tapes to ensure proper wound closure with the characteristics described herein. For instance, PROXI STRIP or a polyester fiber strip (e.g. MERSILENE) may be used.

In certain embodiments, the present fibrin microthread sutures may be used in combination with application of pressure, for example, by occlusive dressing or pressure devices. Application of pressure increases the activity of collagenase, which degrades and remodels the scar tissue thus promoting wound healing. In an embodiment, methods of the invention provides for use of the fibrin microthread in combination with, for example, pressure dressings.

In certain embodiments, the present fibrin microthread sutures may be used in combination with application of a steroid such as cortisone. Steroids increase the collagen degradation activity of collagenase and decrease scar irritation. In an embodiment, the steroid (e.g., corticosteroid or cortisone) is applied topically, for example, as a lotion, ointment, cream, gel, hydrogel, or a tape. In another embodiment, the steroid (e.g., e.g., corticosteroid or cortisone) is injected.

In certain embodiments, the present fibrin microthread sutures may be used in combination with vitamin treatments. Vitamin treatments such as vitamin A, vitamin B, vitamin C, or vitamin E may decrease the expression of collagen forming genes during the healing process and may also soften scars. Vitamin treatment (e.g., vitamin E treatment) may be applied topically using vitamin oil, lotion, cream, ointment, or gel.

In certain embodiments, the present fibrin microthread sutures may be used in combination with silicone. In an embodiment, silicone is applied as silicone-gel plates or sheets. Illustrative silicone-gel plates or sheets include, for example, Dow Corning Silastic Sheeting, Cica-Care (Smith & Nephew), Epi-Derm (Biodermis), Nagosil (Nagor), among others. Silicone may also be applied in the form of topical gel, cream, lotion, and ointment.

In certain embodiments, the present fibrin microthread sutures may be used in combination with physical treatments including, but not limited to, cryotherapy, laser therapy, radiotherapy, collagen induction therapy, or dermabrasion.

In certain embodiments, methods of treating wounds with the present sutures comprises additional steps of, for example, cleaning the wound bed to facilitate wound healing and closure, including, but not limited to: debridement, sharp debridement (surgical removal of dead or infected tissue from a wound), optionally including chemical debriding agents, such as enzymes, to remove necrotic tissue; wound dressings to provide the wound with a moist, warm environment and to promote tissue repair and healing (e.g., wound dressings comprising hydrogels (e.g., AQUASORB®; DUODERM®), hydrocolloids (e.g., AQUACEL®; COMFEEL®), foams (e.g., LYOFOAM®; SPYROSORB®), and alginates (e.g., ALGISITE®; CURASORB®); administration of growth factors to stimulate cell division and proliferation and to promote wound healing e.g. becaplermin.

In various embodiments, methods are provided for promoting wound closure and/or healing of a target tissue, comprising applying the suture of the present invention to a subject in need thereof, wherein the subject has not received a standard of care suture. Examples of standard of care suture includes, but is not limited to, suture comprising silk, linen, nylon, polypropylene, polyamide, polyester, catgut, polyglycolic acid, polyglactin 910, poliglecaprone, or polydioxanone.

In various embodiments, methods are provided for promoting wound closure and/or healing of a target tissue, comprising applying the suture of the present invention to a subject in need thereof, wherein the subject has not received an adjuvant therapy. Examples of adjuvant therapy include but are not limited to, steroid, silicone, vitamin, laser treatment, radiotherapy, pressure dressing, collagen induction therapy, cryotherapy, or dermabrasion.

Kits

In some embodiments, embodiments of the fibrin microthread sutures described herein can be included in kits that can simplify the delivery of the fibrin microthread suture to a target tissue. An illustrative kit of the invention described herein can include a predetermined length of the fibrin microthread suture. The fibrin microthread suture can be wound, coiled, or disposed on a spool. A needle can be coupled to a distal end of the fibrin microthread suture. The needle can include a straight, ¼ circle, ⅜ circle, ½ circle, ⅝ circle, compound curved, half curved (ski), half curved at both ends (canoe), taper, cutting, reverse cutting, trocar point, blunt point, side cutting needle, or any other suitable needle commonly known in the arts. The fibrin microthread suture can be included in the kit in a dehydrated state. A container, for example, a pouch, a vial, a prefilled syringe, a bottle, a carton, or any other suitable container that includes a volume of a hydrating solution can be included in the kit for hydrating the fibrin microthread suture before a ligating procedure. Suitable hydrating solutions can include, for example, a buffer solution (e.g., phosphate buffered saline, HEPES-buffered saline, tris-buffered saline, MES, PIPES), Lactated Ringer's solution, Dulbecco's minimum essential media (DMEM), Ham's F-10 media, Ham's F-12 media, minimum essential media (MEM), any other suitable aqueous solution or combination thereof.

The kit can also include apparatus and devices for performing incisions in a host tissue or assist in implantation of the fibrin microthread sutures into a target tissue. For example, the kit can include one or more scalpels, for example, a number 6 scalpel, a number 9 scalpel, a number 10 scalpel, a number 15 scalpel, any other suitable scalpel or a combination thereof. The scalpel can be provided with the scalpel handle and the scalpel blade coupled together, or disposed separately in the kit such that a user can couple the scalpel blade to the scalpel handle before the surgical procedure. The kit can include a needle holder (e.g., a Mayo-Hegar needle holder, castroviejo needle holder, etc.) and one or more forceps (e.g., artery forceps, atraumatic forceps, biopsy forceps, bulldog forceps, dermal forceps, microsurgery forceps, tissue forceps, any other forceps or combination thereof) to allow facile manipulation of the needle and/or the fibrin microthread suture for implantation into the host tissue. The kit can also include a surgical probe and a skin holder. Furthermore, scissors can be included in the kit, for example, to cut a length of the fibrin microthread sutures.

The kit can include medicaments or compositions to disinfect at least a portion of the host tissue. For example, the kit can include alcohol (e.g., ethyl alcohol), alcohol pads, alcohol wipes, alcohol swabs, anti-septic towels, iodine wipes, or benzoin wipes. The kit can include compositions or materials for dressing the ligated site such as, for example, anti-biotic medicaments (e.g., anti-biotic creams, ointments, or lotions), anti-inflammatory medicaments (e.g., anti-inflammatory creams, ointments, or lotions), surgical pads, cotton gauze, wound closure strips, bandages, surgical tape, or any other medicament or articles that can be used for dressing a ligated site. The kit can further include a label or printed instructions instructing the user on the use of any component included in the kit. The components of the kit can be disposed in a suitable housing for example, a bi-fold bag, a tri-fold bag, or any suitable housing for housing the components of the kit. Each of the components of the kit can be sterilized before disposing in the kit. Suitable sterilization procedures can include, for example, autoclaving, ultraviolet treatment, ethylene oxide treatment, any other sterilization treatment or combination thereof.

The following example is only for illustrative purposes and is not intended to limit the scope of the present disclosure.

EXAMPLES

Example 1

Mechanical Properties of Fibrin Microthread Sutures 12-fiber bundles of fibrin microthreads were assembled into a yarn and their tensile properties evaluated. Prior to testing, samples were hydrated for a minimum of 10 minutes to ensure complete hydration. The threads were anchored into a set of custom grips on an Instron ElectroPuls E1000 designed to mimic those suggested by United States Pharmacopeia (USP) for testing of sutures with a gage length of 2 cm. A single overhand knot was tied in the middle of each sample in keeping with USP suture testing methodology. Samples were then pulled to failure at a strain rate of 4 cm/min, recording load and displacement. Device samples demonstrated consistent properties over n=6 samples. Ultimate load was 1.56±0.11N, strain at failure was 214±58%, stiffness was 49.02±4.54 mN/mm, ultimate tensile strength was 2.26±0.16 MPa, and Young's modulus was calculated to be 14.66±1.23 MPa.

Table 2 below provides a comparison of the Young's moduli of the fibrin microthread suture of the present invention compared to conventional state of art sutures.

TABLE 2

| Tissue Type | Failure Strain | Young's Modulus |
|---|---|---|
| Fibrin Microthread Suture | 215% | 14.7 MPa |
| Cross-linked Collagen | 11.6-15.6% | 383-766 MPa |
| PLGA | 3-10% | 1.4-2.8 GPa |
| PGACL | | 30 GPa |
| Nylon | 68% | 100 MPa |
| Polypropylene | 58% | 100 MPa |

Example 2

Production of Fibrin Microthreads

Fibrin microthreads are produced using a three axis electromechanical extrusion head to "print" fibrin microthreads in a buffer bath (see FIG. 1, panels A-B). The production system allows for the generation of threads with lot-to-lot consistency in both thread diameter and thread failure load (see FIG. 1, panels C and D). The produced fibrin microthreads are used as building blocks for additional products such as sutures.

Example 3

Production of Fibrin Microthread Sutures

Figure 2:
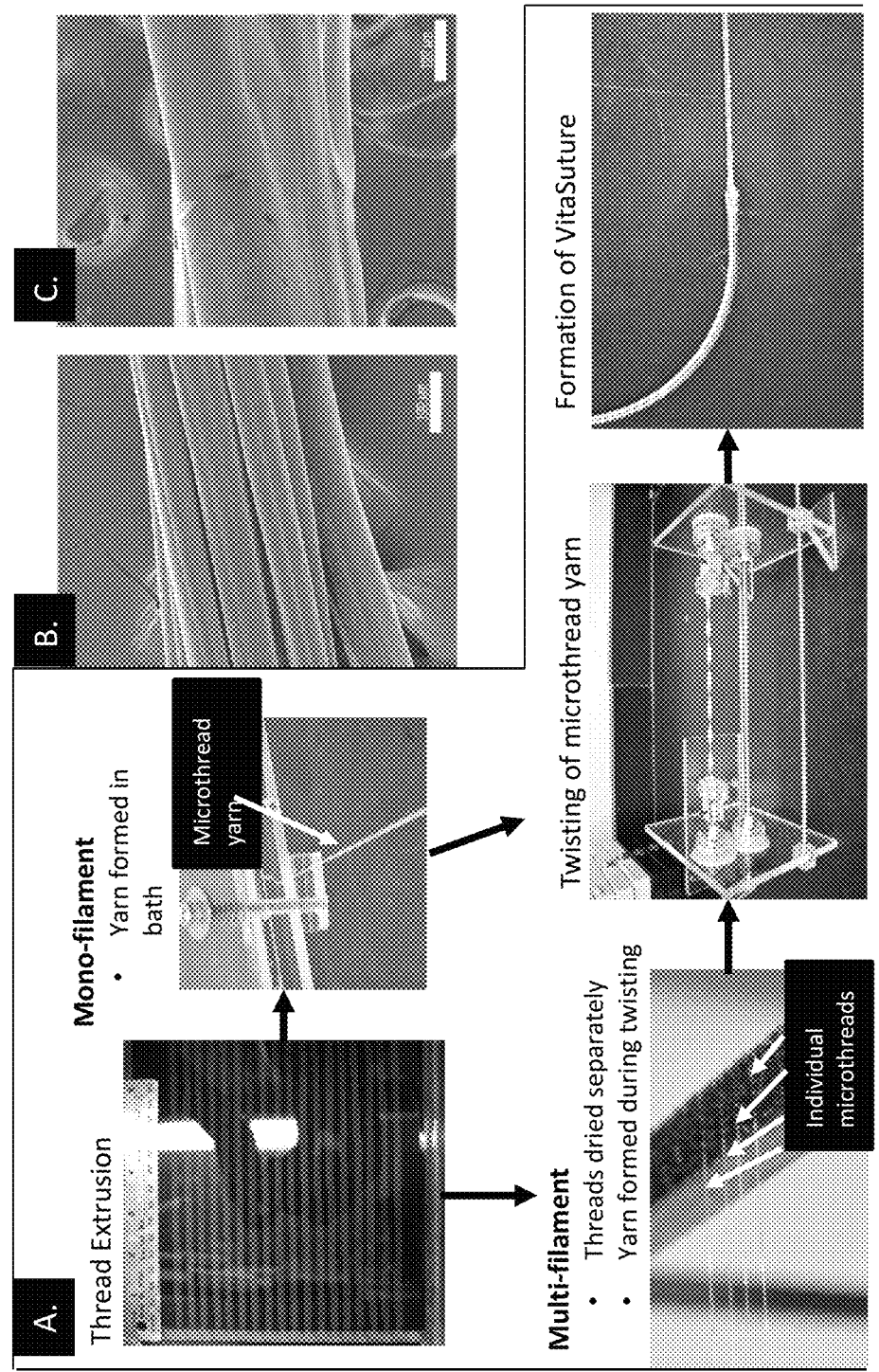
FIG. 2, panels A-C show the production process for multi-filament and mono-filament fibrin microthread sutures.

Suture products can be generated in both a multifilament and monofilament form of varying sizes. Multifilament sutures are formed by fully drying individual microthreads after formation in the bath. Varying numbers of dried threads can then be twisted together with a controlled twist density to produce a multifilament microthread yarn. FIG. 2, panels A-C, differentiate the production process for multi- and mono-filament sutures and show scanning electron micrographs of each type of suture.

Monofilament sutures are produced from the same microthread extrusion process as used for multifilament sutures. Prior to removal from the extrusion bath, varying numbers of microthreads are carefully pulled together in the buffer solution to form a single, cohesive thread. The thread is then removed from the bath and allowed to dry.

Figure 4:
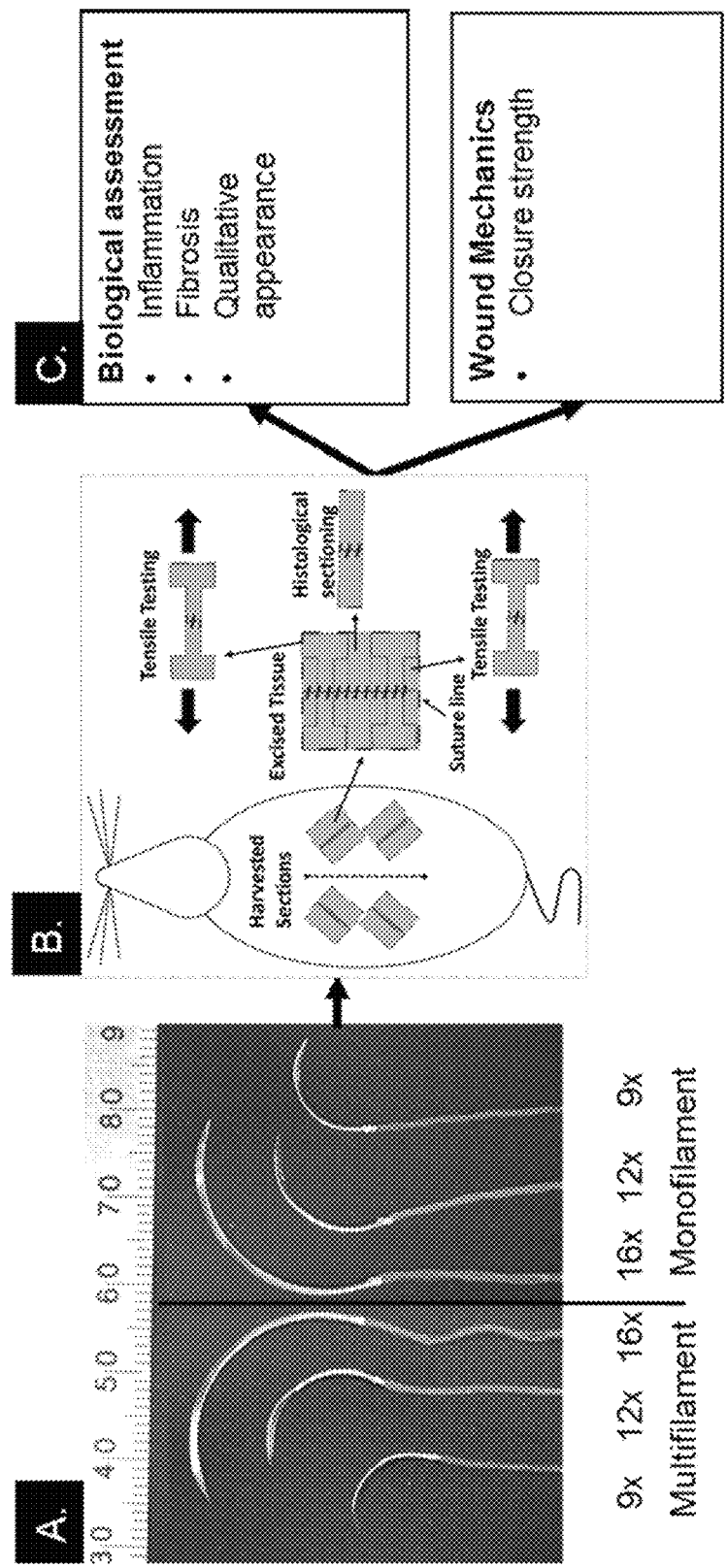
FIG. 4, panels A-C show fibrin microthreads of the invention.

After drying of both the multi- and mono-filaments, sutures are formed by inserting the dried material into the bore hole of a standard drilled-end surgical needle and crimping the suture in place. Use of this process allows for sutures to be readily attached to a variety of needle types for different purposes. See FIG. 4, panels A-D. Sutures are then packaged and sterilized via a standard 12-hour ethylene oxide cycle for use in the sterile operating room.

Example 4

Variation of Fibrin Microthread Mechanics

Methods of manufacturing fibrin microthreads as described herein involve the use of an automated system which produces microthreads of consistent diameter and mechanical strength. To further increase the mechanical strength of the microthreads, various parameters of the microthread extrusion process were modified and tested. Specifically, the fibrin microthreads were assessed mechanically. After formation, dry threads were glued to a piece of vellum paper using silicone glue. Microthreads were rehydrated for at least 10 minutes in lactated ringer's solution and thread diameters were measured using a light microscope. Threads were then tested uniaxially to failure at 200% strain/min on an Instron Electropuls E1000 tensile testing device with a 1 Newton load cell (see FIG. 3, panel A). Results are reported as ultimate tensile strength (MPa) using initial thread diameter and assuming circular cross-section to determine area.

Some of the primary parameters that affect the physical and mechanical properties of fibrin microthreads include the bath composition, the extrusion head velocity, the thrombin and fibrinogen concentrations and the extrusion flow rate. Table 3 below lists the parameters used in an initial microthread extrusion process as well as an improved process with modified parameters for increasing the mechanical strength of the fibrin microthreads used to form sutures ("After" column).

TABLE 3

| Extrusion Parameter | Before | After |
| --- | --- | --- |
| Bath Composition | 10 mM HEPES | 10 mM HEPES + 20 mM $CaCl_3$ |
| Extrusion flow rate | 0.39 mL/min | 0.39 mL/min |
| Fibrinogen concentration | 4.9% Clottable/mL | 4.9% Clottable/mL |
| Thrombin concentration | 30 Units/mL | 60 Units/mL |
| Stretching protocol | 100% out of bath | 100%-rehydrate-200% |

Figure 3:
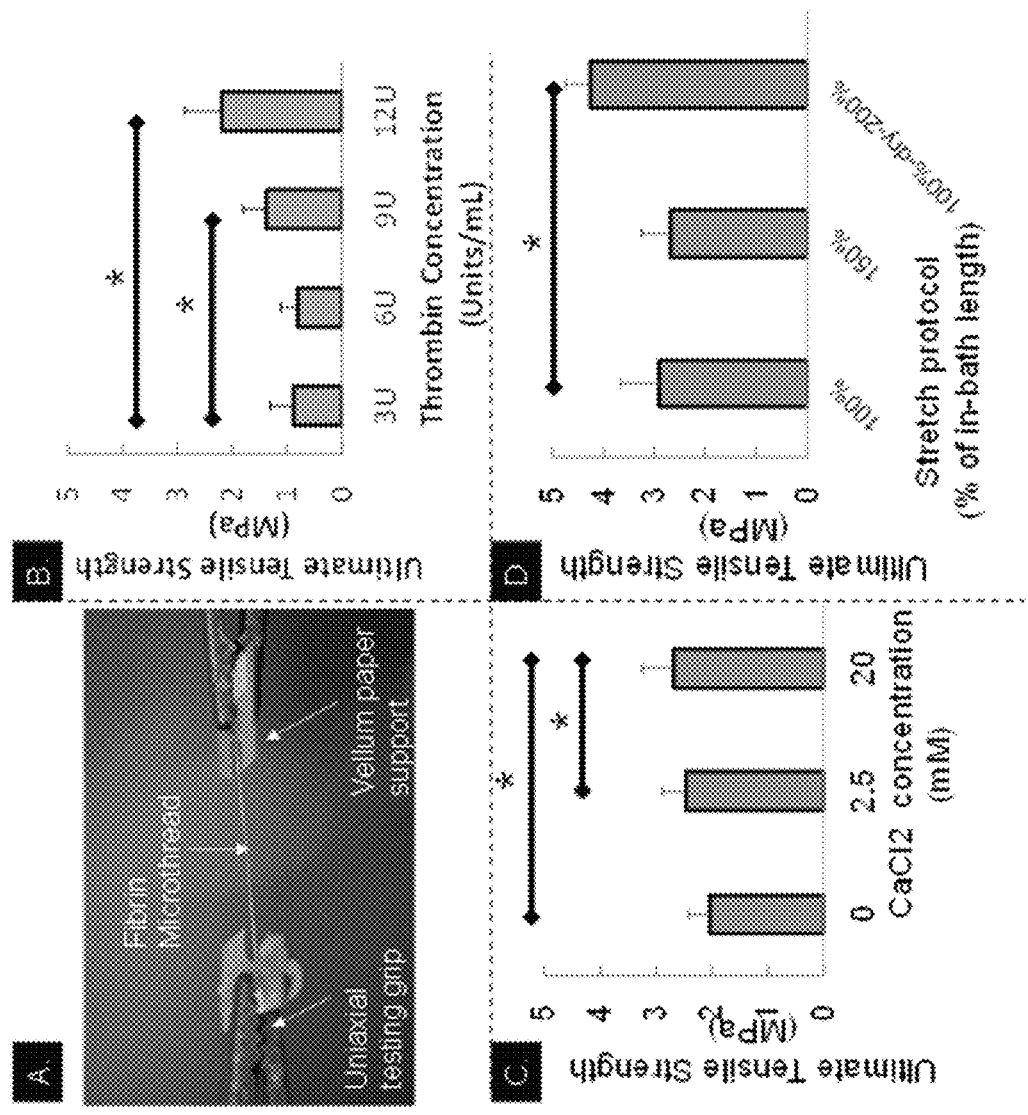
FIG. 3, panels A-D show mechanical characterization of fibrin microthreads.

One of the varied parameters is thrombin concentration. Specifically, threads were produced using the standard extrusion parameters in the "Before" column in Table 3 except varying thrombin concentration. Samples were processed with 3, 6, 9, and 12 U/mL of thrombin, respectively, while maintaining all other parameters constant. Samples were then tested uniaxially to failure. As shown in FIG. 3, panel B, increasing thrombin concentration improved fibrin microthread strength. Further, increasing strength of the fibrin microthreads resulted in an increase in ultimate tensile strength (UTS) compared to initial levels. In particular, a thrombin concentration of 12 units/mL resulted in significant increases in UTS compared to other concentrations.

Another varied parameter is the addition of $CaCl_2$ to the buffer bath. Calcium chloride ($CaCl_2$) may play an important role in fibrinogen polymerization. Accordingly, fibrin microthreads were extruded with different concentrations of $CaCl_2$ in the extrusion bath. Concentrations tested were: 0, 2.5 and 20 mM. After thread formation, threads were tested mechanically. Addition of calcium chloride to the extrusion bath increased thread tensile strength. As shown in FIG. 3, panel C, microthread UTS was significantly increased compared to 0 and low (2.5 mM) concentration of $CaCl_2$ when $CaCl_2$ concentration in the bath was increased to 20 mM.

An additional step of pre-stretching was included into microthread processing. To enhance alignment of fibrin during formation, the initial fibrin microthread production process maintained threads at 100% of their initial length during the drying step of the process. In a first group of this study, a standard 100% stretch protocol was used. In a second group of this study, threads were stretched to 150% of their initial length immediately out of the bath. In the third group, threads were maintained at 100% in bath length and allowed to dry. The threads were then rehydrated in DI water and stretched to 200% in bath length. It was discovered that drying of threads prior to stretching improved thread mechanical strength. Microthread UTS was further increased with the addition of a stretching and drying step to the manufacturing process. The process of drying the threads at 100% in bath length, rehydrating and stretching to 200% in-bath length resulted in a significant ($p<0.05$) increase in thread mechanical strength compared to both 100% in-bath length and 150% in-bath length protocols (see FIG. 3, panel D).

Accordingly, a set of key process variables have been identified which may be used to manipulate the mechanical properties of fibrin microthreads. By modulating one or more of these variables, the ultimate tensile strength of the fibrin microthreads are increased. These experimental procedures demonstrate that the mechanical characteristics of fibrin microthreads can be improved without employing cross-linking agents or harsh reaction conditions.

Example 5

Mechanics of Monofilament Fibrin Microthread

12× monofilament sutures (n=11) were produced as described above. Devices were hydrated for a minimum of 1 hour in lactated Ringer's solution to fully hydrate, and loaded onto spring loaded grips. Samples were then tested to uniaxial failure under straight pull using a 50N load cell on an Instron ElectroPuls E1000.

Ultimate load for the 11 tested sutures was 2.42±0.42 N. The mechanical behavior illustrated a load at failure that was stronger than USP requirements for 6-0 surgical gut suture. The results of this analysis suggest that the mechanical properties of 12×, and possibly smaller, suture configurations are at least comparable to those of surgical gut.

Example 6

Monofilament Thread Assembly

Aqueous fibrinogen solution and a thrombin are co-extruded using the previously described microthread extrusion equipment in a saline bath containing standard HEPES buffer and $CaCl_2$. Concentration ranges previously described remain appropriate. The machine is programmed in such a fashion that it traces a similar pattern in the bath such that multiple layers of fibrin are deposited. Typical time between layer depositions over a given point are approximately 15 seconds. Conditions have also been evaluated using longer periods of time, for example, approximately 3 minutes. Either condition forms a monofilament fibrin thread.

Methods as described herein can produce a single layer of deposition. Methods as described herein can also produce a 12-layer deposition to form a monofilament fibrin thread which may be used in suture applications. Monofilament fibrin threads formed from 3, 6, 9, 10, 12, and 14-layer depositions have also been produced.

These monofilament threads post-extrusion may be stretched mechanically in order to increase their ultimate tensile strength either prior to bath removal (in-bath) or following bath removal. For example, the monofilament thread may be stretched in-bath for 6-8 minutes following initiation of extrusion on a particular point.

If stretching, it is desirable to stretch these threads within 30 or more minutes of initiating extrusion or under 2 minutes. Threads may also be stretched within 10-30 minutes of initiating extrusion or 2-6 minutes. In addition, threads may also be stretched within 6-8 minutes of initiating extrusion. The amount of time for stretching varies depending on ease of handling the materials and their resultant mechanical properties.

Stretching may be varied between 100-250%. For example, the monofilament thread may be stretched to 200%.

Following a stretching step, resultant monofilament materials may be twisted to improve overall cross-sectional uniformity. Twisting may be performed to a level of between 0.1 twists/cm to around 3 twists/cm. For example, twisting may be performed at 1 twist/cm prior to drying.

Following stretching (with or without twisting), the resultant fibrin materials are dried under ambient conditions. For example, drying may take approximately 6 hours.

Following drying, a bored-end needle may be attached to the fibrin monofilament via a standard crimping mechanism to generate a suture. Alternatively, the threads may be passed through the eyelet of an eyelet-style needle, then rehydrated in a saline buffer and hereby attached and appropriately organized. For example, bored-end needles or eyelet-style needles may be crimped on at this stage.

In the case where an eyelet-style needle is used, additional twisting may be applied post-needle attachment to further organize the suture yarn. Twisting may be performed to a level of between 0.1 twists/cm to around 3 twists/cm. In certain instances, twisting may be performed in a direction counter to any initial twisting applied to the yarn, generating a balanced yarn.

Provided below in Table 4 is a characterization data of a 10-pass fibrin monofilament thread stretched 6-8 minutes post-extrusion.

Threads were subjected to single-pull-to-failure testing using an Instron 3342 test system with a 50N load cell and pneumatic yarn grips. A gauge length of 55 mm was used and a strain rate of 200% per minute. Maximum load and extension at failure were both recorded. Prior to testing, sample diameters were measured in order to calculate ultimate tensile strength.

Dry diameter is recorded using a Willrich 65-0642Q digital yarn micrometer featuring an AQD-2600N digital indicator according to USP 29.861. Briefly, for dry diameter measurement a monofilament was placed under ambient conditions between the platens of the yarn micrometer under a compressive load of 210 g spread over the platen area, a circular foot 12.7 mm in diameter. Hydrated diameter measurement was performed in the same fashion as dry diameter measurement with the exception of the fact that fibrin monofilaments were first incubated for a minimum of 10 and a maximum of 30 minutes in and excess of lactated Ringer's solution.

TABLE 4

Representative Physical Properties for a 10x Layered Fibrin Monofilament

| Maximum Load (N) | | Maximum Extension (mm) | | Dry Diameter (microns) | | Hydrated Diameter (microns) | | Ultimate Tensile Strength (N/mm2 based on hydrated diameter) | | Young's Modulus (Mpa based on hydrated diameter) | |
|---|---|---|---|---|---|---|---|---|---|---|---|
| Mean | Standard Deviation | Mean | Standard Deviation | Mean | Standard Deviation | Mean | Standard Deviation | Mean | Standard Deviation | Mean | Standard Deviation |
| 2.011 | 0.426 | 92.535 | 13.153 | 443.755 | 42.479 | 334.000 | 18.660 | 22.721 | 3.792 | 8.536 | 1.545 |

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%. In another example, about 250 μm would include 225 μm to 275 μm, about 1,000 μm would include 900 μm to 1,100 μm.

In various embodiments, the terms "fibrin microthread" and "fibrin microthread sutures" may be used interchangeably to refer to the sutures which comprise fibrin microthreads.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

Equivalents

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for promoting wound closure and/or healing of a target tissue in a subject, comprising applying a monofilament suture to the target tissue, wherein the monofilament is:
   a cohesive fibrin-based thread which mimics the stiffness behavior and elasticity of the target tissue and
   is produced in a buffer solution.

2. The method of claim 1, wherein the suture exhibits a stiffness of about 5 MPa to about 20 MPa as measured by Young's modulus.

3. The method of claim 1, wherein the suture is associated with one or more of a substrate or a physiologically acceptable patch, a dressing, a bandage, or a natural or mechanical valve.

4. The method of claim 1, wherein the target tissue is a soft tissue selected from skin, tendon, ligament, fascia, fibrous tissue, fat, synovial membrane, and muscle, nerve and blood vessel.

5. The method of claim 4, wherein the soft tissue is skin.

6. The method of claim 1, wherein the target tissue is hypertrophic or swollen.

7. The method of claim 1, wherein the wound is a surgical wound.

8. The method of claim 7, wherein the surgical wound results from aesthetic surgery.

9. The method of claim 7, wherein the surgical wound results from skin grafting.

10. The method of claim 1, wherein the wound is a trauma wound.

11. A method for promoting wound closure and/or healing of a target tissue, comprising applying a monofilament suture to the target tissue of a subject,
wherein the monofilament is a cohesive fibrin-based thread which mimics the stiffness behavior and elasticity of the target tissue and is produced in a buffer solution, and
wherein the subject has not received a standard of care suture.

12. The method of claim 11, wherein the standard of care suture comprises silk, linen, nylon, polypropylene, polyamide, polyester, catgut, polyglycolic acid, polyglactin 910, poliglecaprone, or polydioxanone.

13. A method for promoting wound closure and/or healing of a target tissue, comprising applying a monofilament suture to the target tissue of a subject,
wherein the monofilament is a cohesive fibrin-based thread which mimics the stiffness behavior and elasticity of the target tissue and is produced in a buffer solution, and
wherein the subject has not received an adjuvant therapy.

14. The method of claim 13, wherein the adjuvant therapy is selected from steroid, silicone, vitamin, laser treatment, radiotherapy, pressure dressing, collagen induction therapy, cryotherapy, or dermabrasion.

15. The method of claim 1, wherein the monofilament suture is not a multifilament fibrin microthread.

* * * * *